(12) United States Patent
Darlington et al.

(10) Patent No.: US 9,248,318 B2
(45) Date of Patent: Feb. 2, 2016

(54) OPTIMIZATION AND FEEDBACK CONTROL OF HIFU POWER DEPOSITION THROUGH THE ANALYSIS OF DETECTED SIGNAL CHARACTERISTICS

(75) Inventors: Gregory P. Darlington, Snohomish, WA (US); Charles D. Emery, Issaquah, WA (US); Justin A. Reed, Seattle, WA (US); Barry Friemel, Redmond, WA (US)

(73) Assignee: Mirabilis Medica Inc., Bothell, WA (US)

( * ) Notice: Subject to any disclaimer, the term of this patent is extended or adjusted under 35 U.S.C. 154(b) by 236 days.

(21) Appl. No.: 12/537,217

(22) Filed: Aug. 6, 2009

(65) Prior Publication Data

US 2010/0036292 A1 Feb. 11, 2010

Related U.S. Application Data

(63) Continuation-in-part of application No. 12/187,318, filed on Aug. 6, 2008.

(60) Provisional application No. 61/180,187, filed on May 21, 2009.

(51) Int. Cl.
*A61H 1/00* (2006.01)
*A61N 7/02* (2006.01)
(Continued)

(52) U.S. Cl.
CPC ......... *A61N 7/02* (2013.01); *A61B 2017/00106* (2013.01); *A61B 2019/5276* (2013.01)

(58) Field of Classification Search
CPC .................................. A61N 7/00; A61N 7/02
USPC .......................................... 601/2–4; 600/439
See application file for complete search history.

(56) References Cited

U.S. PATENT DOCUMENTS

| 3,470,868 A | 10/1969 | Krause |
| 3,480,002 A | 11/1969 | Flaherty |
| 3,676,584 A | 7/1972 | Plakas |

(Continued)

FOREIGN PATENT DOCUMENTS

| EP | 0301360 B1 | 2/1989 |
| EP | 0614651 A1 | 9/1994 |

(Continued)

OTHER PUBLICATIONS

International Search Report and Written Opinion mailed May 18, 2010, in corresponding International Application No. PCT/US2009/053050, filed Aug. 6, 2009, 15 pages.

(Continued)

*Primary Examiner* — Tse Chen
*Assistant Examiner* — Hien Nguyen
(74) *Attorney, Agent, or Firm* — Seed IP Law Group PLLC

(57) ABSTRACT

A system and method for adjusting or selecting the treatment parameters for HIFU signals to treat a target treatment site, and/or to aid in visualizing the likely degree and location of HIFU effects on patient tissue. The system transmits one or more test signals into patient tissue and receives signals created in response to the test signals. The signals are analyzed to determine a response curve of how a characteristic of the signal varies with the one or more test signals. The response curve of the detected signals is used to select a treatment parameter.

43 Claims, 27 Drawing Sheets

(51) Int. Cl.
  *A61B 17/00*  (2006.01)
  *A61B 19/00*  (2006.01)

(56) References Cited

U.S. PATENT DOCUMENTS

| | | |
|---|---|---|
| 3,941,112 A | 3/1976 | Habert |
| 4,059,098 A | 11/1977 | Murdock |
| 4,097,835 A | 6/1978 | Green |
| 4,185,502 A | 1/1980 | Frank |
| 4,282,755 A | 8/1981 | Gardineer |
| 4,347,850 A | 9/1982 | Kelly-Fry |
| 4,484,569 A | 11/1984 | Driller |
| 4,742,829 A | 5/1988 | Law |
| 4,756,313 A | 7/1988 | Terwilliger |
| 4,819,621 A | 4/1989 | Ueberle |
| 4,835,689 A | 5/1989 | O'Donnell |
| 4,858,613 A | 8/1989 | Fry |
| 4,865,042 A | 9/1989 | Umemura |
| 4,893,624 A | 1/1990 | Lele |
| 4,932,414 A | 6/1990 | Coleman |
| 5,005,579 A | 4/1991 | Wurster |
| 5,036,855 A | 8/1991 | Fry |
| 5,070,879 A | 12/1991 | Herres |
| 5,080,101 A | 1/1992 | Dory |
| 5,080,102 A | 1/1992 | Dory |
| 5,080,660 A | 1/1992 | Buelna |
| 5,117,832 A | 6/1992 | Sanghvi |
| 5,234,429 A | 8/1993 | Goldhaber |
| 5,271,402 A | 12/1993 | Yeung |
| 5,391,140 A | 2/1995 | Schaetzle |
| 5,441,499 A | 8/1995 | Fritzsch |
| 5,471,988 A | 12/1995 | Fujio |
| 5,474,071 A | 12/1995 | Chapelon |
| 5,492,126 A | 2/1996 | Hennige |
| 5,520,188 A | 5/1996 | Hennige |
| 5,558,092 A | 9/1996 | Unger |
| 5,619,999 A | 4/1997 | Von Behren |
| 5,666,954 A | 9/1997 | Chapelon |
| 5,720,287 A | 2/1998 | Chapelon |
| 5,762,066 A | 6/1998 | Law |
| 5,769,790 A | 6/1998 | Watkins |
| 5,810,007 A | 9/1998 | Holupka |
| 5,882,302 A | 3/1999 | Driscoll, Jr. |
| 5,976,092 A | 11/1999 | Chinn |
| 5,984,881 A | 11/1999 | Ishibashi |
| 5,993,389 A | 11/1999 | Driscoll, Jr. |
| 6,002,251 A | 12/1999 | Sun |
| 6,007,499 A | 12/1999 | Martin |
| 6,042,556 A | 3/2000 | Beach |
| 6,050,943 A | 4/2000 | Slayton |
| 6,071,239 A | 6/2000 | Cribbs |
| 6,083,159 A | 7/2000 | Driscoll, Jr. |
| 6,126,607 A | 10/2000 | Whitmore, III |
| 6,196,972 B1 | 3/2001 | Moehring |
| 6,217,530 B1 | 4/2001 | Martin |
| 6,254,601 B1 | 7/2001 | Burbank |
| 6,267,734 B1* | 7/2001 | Ishibashi et al. ............ 601/2 |
| 6,315,741 B1 | 11/2001 | Martin |
| 6,390,973 B1 | 5/2002 | Ouchi |
| 6,425,867 B1 | 7/2002 | Vaezy |
| 6,432,067 B1 | 8/2002 | Martin |
| 6,451,013 B1 | 9/2002 | Bays |
| 6,461,314 B1 | 10/2002 | Pant |
| 6,488,639 B1 | 12/2002 | Ribault |
| 6,500,133 B2 | 12/2002 | Martin |
| 6,508,774 B1 | 1/2003 | Acker |
| 6,537,224 B2 | 3/2003 | Mauchamp |
| 6,602,251 B2 | 8/2003 | Burbank |
| 6,613,004 B1 | 9/2003 | Vitek |
| 6,626,855 B1 | 9/2003 | Weng |
| 6,632,177 B1 | 10/2003 | Phillips |
| 6,633,658 B1 | 10/2003 | Dabney |
| 6,645,162 B2 | 11/2003 | Friedman |
| 6,666,822 B2 | 12/2003 | Agano |
| 6,666,835 B2 | 12/2003 | Martin |
| 6,676,601 B1 | 1/2004 | Lacoste |
| 6,692,450 B1 | 2/2004 | Coleman |
| 6,716,184 B2 | 4/2004 | Vaezy |
| 6,719,694 B2 | 4/2004 | Weng |
| 6,740,082 B2 | 5/2004 | Shadduck |
| 6,764,488 B1 | 7/2004 | Burbank |
| 6,837,855 B1 | 1/2005 | Puech |
| 6,840,936 B2 | 1/2005 | Sliwa, Jr. |
| 6,936,046 B2 | 8/2005 | Hissong |
| 7,061,381 B2 | 6/2006 | Forcier |
| 7,063,666 B2 | 6/2006 | Weng |
| 7,105,007 B2 | 9/2006 | Hibler |
| 7,175,596 B2 | 2/2007 | Vitek |
| 7,258,674 B2 | 8/2007 | Cribbs |
| 7,286,499 B2 | 10/2007 | Tiedemann, Jr. |
| 7,452,357 B2 | 11/2008 | Voegele |
| 7,470,241 B2 | 12/2008 | Weng |
| 7,473,224 B2 | 1/2009 | Makin |
| 7,674,630 B2 | 3/2010 | Siversson |
| 7,699,782 B2 | 4/2010 | Angelsen |
| 7,993,289 B2 | 8/2011 | Quistgaard |
| 8,016,757 B2 | 9/2011 | Kaczkowski |
| 2001/0012934 A1 | 8/2001 | Chandrasekaran |
| 2001/0017848 A1* | 8/2001 | Tiedemann, Jr. ............ 370/318 |
| 2002/0029036 A1 | 3/2002 | Goble |
| 2002/0065512 A1 | 5/2002 | Fjield |
| 2002/0120192 A1* | 8/2002 | Nolte et al. ................. 600/424 |
| 2002/0120259 A1 | 8/2002 | Lettice |
| 2002/0147397 A1* | 10/2002 | Agano ......................... 600/437 |
| 2003/0004439 A1 | 1/2003 | Pant |
| 2003/0060736 A1 | 3/2003 | Martin |
| 2003/0149380 A1 | 8/2003 | Fujimoto |
| 2003/0189488 A1* | 10/2003 | Forcier et al. .............. 340/572.1 |
| 2003/0233045 A1 | 12/2003 | Vaezy |
| 2004/0030268 A1 | 2/2004 | Weng |
| 2004/0030269 A1 | 2/2004 | Horn |
| 2004/0039312 A1* | 2/2004 | Hillstead et al. .................. 601/2 |
| 2004/0082859 A1 | 4/2004 | Schaer |
| 2004/0153126 A1 | 8/2004 | Okai |
| 2004/0242999 A1 | 12/2004 | Vitek |
| 2004/0243201 A1 | 12/2004 | Goldman |
| 2005/0038340 A1 | 2/2005 | Vaezy |
| 2005/0085726 A1 | 4/2005 | Lacoste |
| 2005/0101854 A1 | 5/2005 | Larson |
| 2005/0107702 A1 | 5/2005 | He |
| 2005/0154431 A1 | 7/2005 | Quistgaard |
| 2005/0203399 A1 | 9/2005 | Vaezy |
| 2005/0256405 A1 | 11/2005 | Makin |
| 2005/0267454 A1 | 12/2005 | Hissong |
| 2005/0281444 A1 | 12/2005 | Lundberg |
| 2006/0052701 A1 | 3/2006 | Carter |
| 2006/0056273 A1* | 3/2006 | Scoca et al. ..................... 367/99 |
| 2006/0264748 A1 | 11/2006 | Vaezy |
| 2007/0010805 A1 | 1/2007 | Fedewa |
| 2007/0016042 A1 | 1/2007 | Kawabata |
| 2007/0066990 A1 | 3/2007 | Marsella |
| 2007/0083120 A1 | 4/2007 | Cain |
| 2007/0106157 A1 | 5/2007 | Kaczkowski |
| 2007/0167798 A1 | 7/2007 | Cai |
| 2007/0194658 A1 | 8/2007 | Zhang |
| 2007/0197918 A1 | 8/2007 | Vitek |
| 2007/0238994 A1 | 10/2007 | Stecco |
| 2007/0239011 A1 | 10/2007 | Lau |
| 2007/0255267 A1 | 11/2007 | Diederich |
| 2007/0270792 A1 | 11/2007 | Hennemann |
| 2008/0039724 A1 | 2/2008 | Seip |
| 2008/0058683 A1 | 3/2008 | Gifford |
| 2008/0071165 A1 | 3/2008 | Makin |
| 2008/0086036 A1 | 4/2008 | Hartley |
| 2008/0125771 A1 | 5/2008 | Lau |
| 2008/0154131 A1 | 6/2008 | Lee |
| 2008/0217259 A1 | 9/2008 | Siversson |
| 2008/0221647 A1 | 9/2008 | Chamberland |
| 2008/0253525 A1* | 10/2008 | Boyden et al. ................... 378/87 |
| 2008/0281314 A1 | 11/2008 | Johnson |
| 2008/0319436 A1 | 12/2008 | Daniel |
| 2009/0000626 A1* | 1/2009 | Quaid et al. .................... 128/898 |
| 2009/0036774 A1 | 2/2009 | Weng |

(56) References Cited

U.S. PATENT DOCUMENTS

| | | | |
|---|---|---|---|
| 2009/0069677 | A1 | 3/2009 | Chen |
| 2009/0228001 | A1 | 9/2009 | Pacey |
| 2009/0326420 | A1 | 12/2009 | Moonen |

FOREIGN PATENT DOCUMENTS

| | | | |
|---|---|---|---|
| EP | 0734742 | A2 | 10/1996 |
| EP | 1 726 267 | A2 | 11/2006 |
| GB | 2 279 742 | A | 1/1995 |
| JP | 58-173539 | A | 10/1983 |
| JP | 405023336 | A | 2/1993 |
| JP | 11-313833 | A | 11/1999 |
| JP | 2001-253836 | A | 9/2001 |
| JP | 2001-526076 | A | 12/2001 |
| JP | 2006-204929 | A | 8/2006 |
| JP | 2007-144183 | A | 6/2007 |
| WO | 93/17646 | A2 | 9/1993 |
| WO | 94/27502 | A1 | 12/1994 |
| WO | 95/20360 | A1 | 8/1995 |
| WO | 97/00646 | A1 | 1/1997 |
| WO | 00/45706 | A1 | 8/2000 |
| WO | 01/71380 | A2 | 9/2001 |
| WO | 01/82777 | A2 | 11/2001 |
| WO | 02/100486 | A1 | 12/2002 |
| WO | 2004/073524 | A1 | 9/2004 |
| WO | 2005/000097 | A2 | 1/2005 |
| WO | 2006/097661 | A1 | 9/2006 |
| WO | 2006/129099 | A1 | 12/2006 |

OTHER PUBLICATIONS

Annex to Form PCT/ISA/206, Communication Relating to the Results of the Partial International Search mailed Dec. 15, 2009, in corresponding International Application No. PCT/US2009/053050, filed Aug. 6, 2009.
Daum, D.R., and K. Hynynen, "A 256-Element Ultrasonic Phased Array System for the Treatment of Large Volumes of Deep Seated Tissue," IEEE Transactions on Ultrasonics, Ferroelectrics, and Frequency Control 46(5):1254-1268, Sep. 1999.
Enholm, J.K., et al., "Improved Volumetric MR-HIFU Ablation by Robust Binary Feedback Control," IEEE Transactions on Biomedical Engineering 57(1):103-113, Jan. 2010.
Mougenot, C., et al., "Automatic Spatial and Temporal Temperature Control for MR-Guided Focused Ultrasound Using Fast 3D MR Thermometry and Multispiral Trajectory of the Focal Point," Magnetic Resonance in Medicine 52(5):1005-1015, Nov. 2004.
Mougenot, C., et al., "Three-Dimensional Spatial and Temporal Temperature Control with MR Thermometry-Guided Focused Ultrasound (MRgHIFU)," Magnetic Resonance in Medicine 61(3):603-614, Mar. 2009.
Ngo, F.C., et al., "An Experimental Analysis of a Sector-Vortex Phased Array Prototype," Proceedings of the IEEE Ultrasonics Symposium, Montreal, Oct. 3-6, 1989, vol. 2, pp. 999-1002.
Rabkin, B.A., et al., "Hyperecho in Ultrasound Images of HIFU Therapy: Involvement of Cavitation," Ultrasound in Medicine & Biology 31(7):947-956, Jul. 2005.
Umemura, S.-I., and C.A. Cain, "Acoustical Evaluation of a Prototype Sector-Vortex Phased-Array Applicator," IEEE Transactions on Ultrasonics, Ferroelectrics, and Frequency Control 39(1):32-38, Jan. 1992.
Extended European Search Report mailed Feb. 26, 2010, issued in European Patent Application No. 07811847.8, filed Apr. 13, 2007, 7 pages.
International Search Report mailed May 11, 2010, issued in International Application No. PCT/US2009/059589, filed Oct. 5, 2009, 5 pages.
International Search Report and Written Opinion mailed Oct. 26, 2010, issued in International Application No. PCT/US2010/026565, filed Mar. 8, 2010, 10 pages.
Cain, C.A., and S.-I. Umemura, "Concentric-Ring and Sector-Vortex Phased-Array Applicators for Ultrasound Hyperthermia," IEEE Transactions on Microwave Theory and Techniques 34(5):542-551, May 1986.

Chapelon, J.Y., et al., "The Feasibility of Tissue Ablation Using High Intensity Electronically Focused Ultrasound," Proceedings of the IEEE Ultrasonics Symposium 1993, Baltimore, Oct. 31 - Nov. 3, 1993, pp. 1211-1214.
Chen, L., et al., "Effect of Blood Perfusion on the Ablation of Liver Parenchyma with High-Intensity Focused Ultrasound," Physics in Medicine and Biology 38(11):1661-1673, Nov. 1993.
Cheng, S.-Q., et al., "High-Intensity Focused Ultrasound in the Treatment of Experimental Liver Tumour," Journal of Cancer Research and Clinical Oncology 123(4):219-223, Apr. 1997.
Coad, J.E., "Thermal Fixation: A Central Outcome of Hyperthermic Therapies," Proceedings of the SPIE Conference on Thermal Treatment of Tissue: Energy Delivery and Assessment III 5698:15-22, San Jose, Calif., Jan. 23, 2005.
Delon-Martin, C., et al., "Venous Thrombosis Generation by Means of High-Intensity Focused Ultrasound," Ultrasound in Medicine & Biology 21(1):113-119, 1995.
Friedland, F., "Ultrasonic Therapy," American Journal of Nursing 59(9):1272-1275, Sep. 1959.
Fry, F.J., "Recent Bioeffects with Ultrasound on the Reproductive System and Solid Tumors," Journal of the Acoustical Society of America 63(Suppl. 1):S13, May 1978.
Hallberg, L., et al., "Menstrual Blood Loss—A Population Study: Variation at Different Ages and Attempts to Define Normality," Acta Obstetricia et Gynecologica Scandinavica 45(3):320-351, 1966.
International Search Report dated Jun. 26, 2009, issued in International Application No. PCT/US2008/082829, filed Jul. 11, 2008.
Lee, J.M., et al., "Comparison of Wet Radiofrequency Ablation With Dry Radiofrequency Ablation and Radiofrequency Ablation Using Hypertonic Saline Preinjection: Ex Vivo Bovine Liver," Korean Journal of Radiology 5(4):258-265, Dec. 2004.
Lee, J.M., et al., "Wet Radio-Frequency Ablation Using Multiple Electrodes: Comparative Study of Bipolar Versus Monopolar Modes in the Bovine Liver," European Journal of Radiology 54:408-417, Jun. 2005.
Mittleman, R.S., et al., "Use of the Saline Infusion Electrode Catheter for Improved Energy Delivery and Increased Lesion Size in Radiofrequency Catheter Ablation," Pacing and Clinical Electrophysiology 18(5):953-1081, May 1995, Part I.
Orsini-Meinhard, K., "UW Tech-Transfer Program Putting Discoveries to Work," The Seattle Times, May 27, 2007.
Rabkin, B.A., "Biological and Physical Mechanisms of HIFU-Induced Hyperecho in Ultrasound Images," Ultrasound in Medicine & Biology 32(11)1721-1729, Nov. 2006.
Sanghvi, N.T., "High Intensity Focused Ultrasound (HIFU) for the Treatment of Rectal Tumors: A Feasibility Study," Proceedings of IEEE Ultrasonics Symposium 3:1895-1898, Cannes, France, Nov. 1-4, 1994.
"ThermoDox™ Animal Studies to Be Presented at 6th International Symposium on Therapeutic Ultrasound in Oxford, England," Aug. 30 - Sep. 2, 2006, Celsion, Inc.,<http://www.celsion.com/news/releasedetail.dfm> [retrieved Oct. 8, 2007], 2 pages.
"ThermoDox™ : Heat-Activated Liposome Drug," © 2007 Celsion, Inc., <http://www.celsion.com/products/ThermoDox.cfm> [retrieved Oct. 8, 2007], 3 pages.
Vaezy, S., et al., "Image-Guided Acoustic Therapy," Annual Review of Biomedical Engineering 3:375-390, Aug. 2001.
Winter, T.C., et al., "Focal Tumor Ablation: A New Era in Cancer Therapy," Ultrasound Quarterly 22(3):204-209, Sep. 2006.
Zanelli, C.I., et al., "Design and Characterization of a 10 cm Annular Array Transducer for High Intensity Focused Ultrasound (HIFU) Applications," Proceedings of the IEEE Ultrasonics Symposium 3:1887-1890, Cannes, France, Nov. 1-4, 1994.
European Office Action dated Sep. 17, 2013, in European Application No. 09 791 246.3, filed Aug. 6, 2009, 4 pages.
International Search Report mailed Jun. 8, 2010, issued in International Application No. PCT/US2009/082127, filed Oct. 26, 2009, 3 pages.
Japanese Notice of Reasons for Rejection mailed Sep. 3, 2013, in corresponding Japanese Patent Application No. 2011 522254, filed Aug. 6, 2009, 10 pages.

* cited by examiner

Fig. 8.

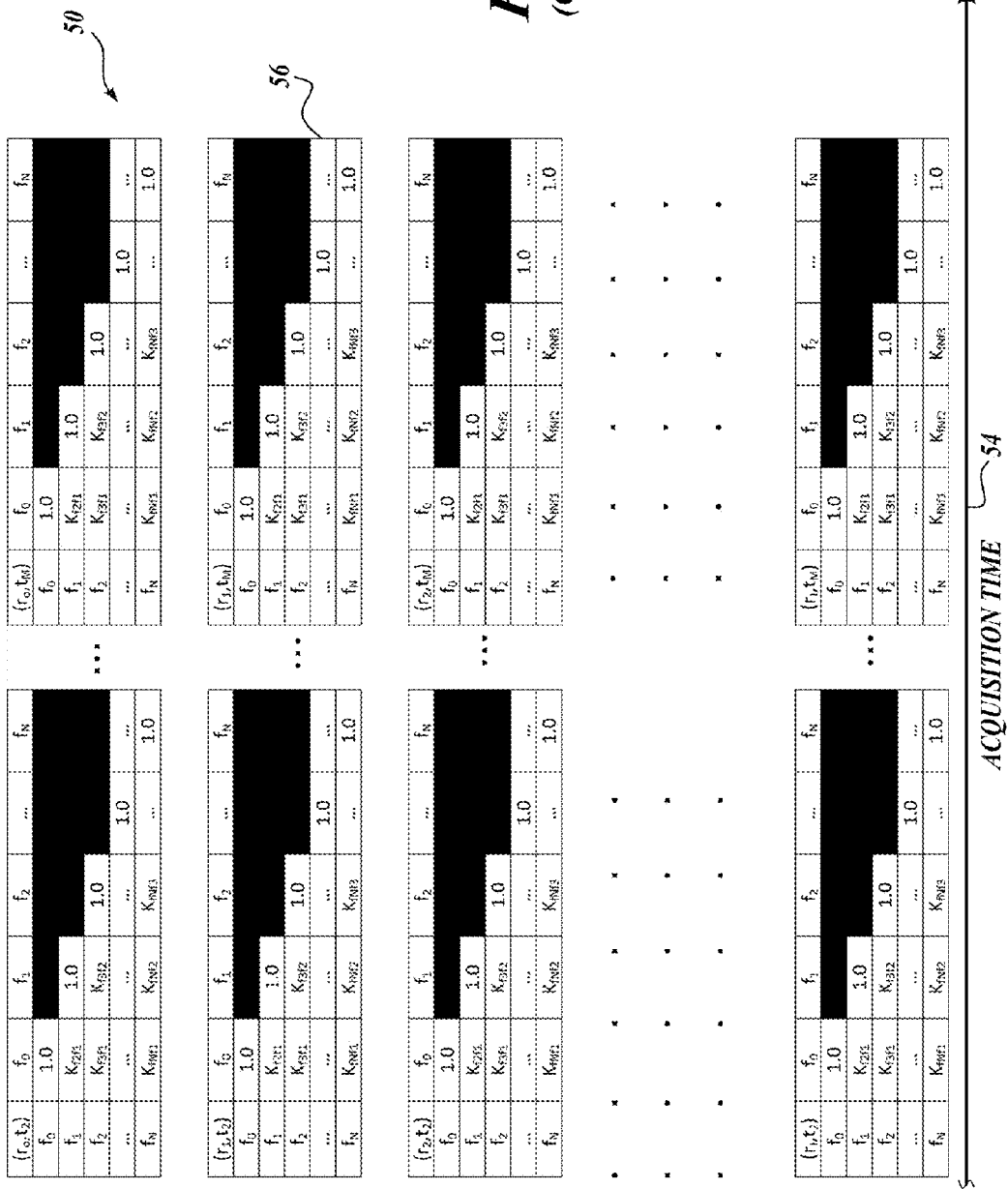

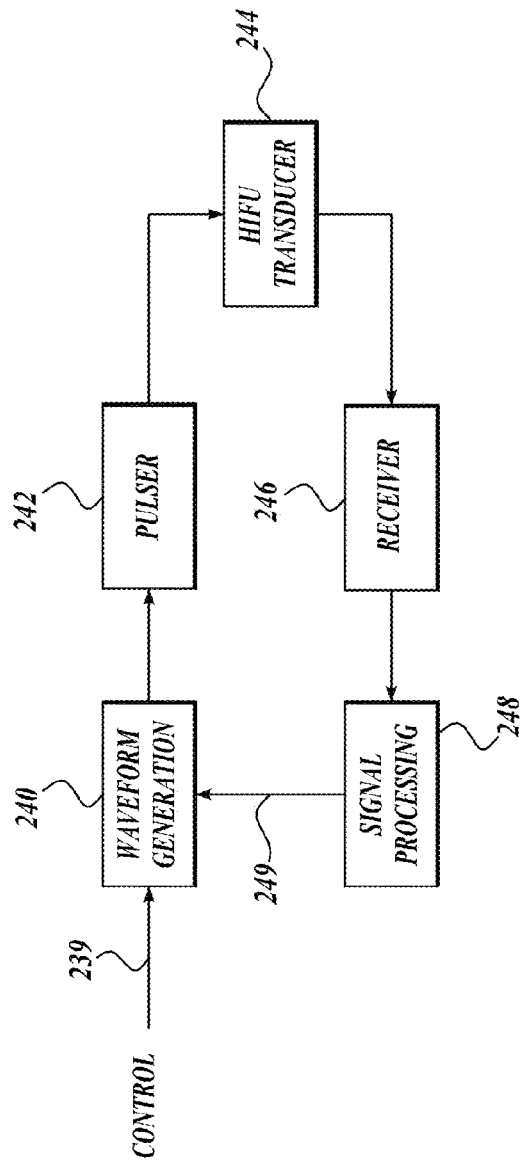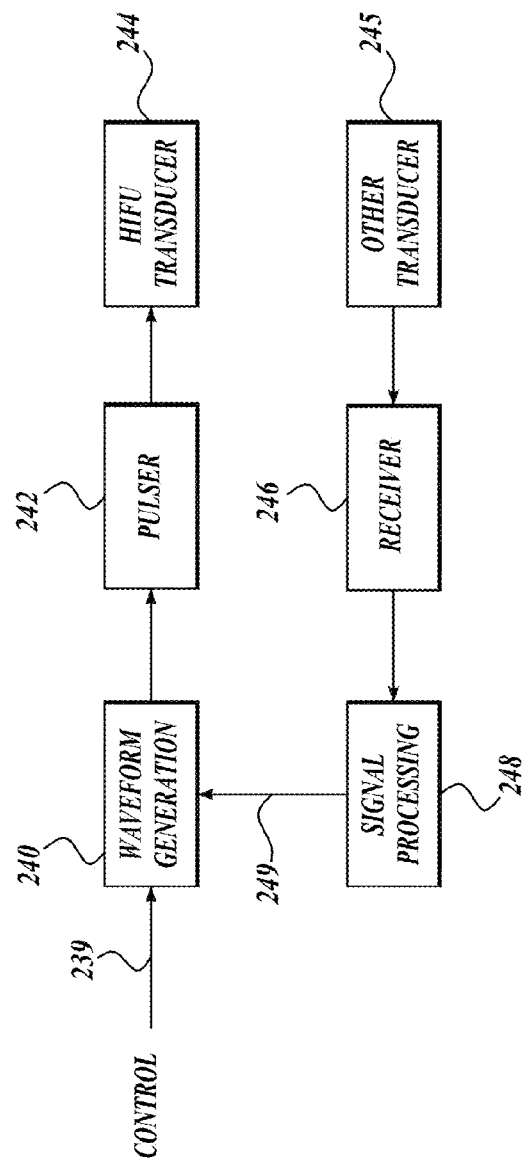

OPTIMIZATION AND FEEDBACK CONTROL OF HIFU POWER DEPOSITION THROUGH THE ANALYSIS OF DETECTED SIGNAL CHARACTERISTICS

CROSS-REFERENCES TO RELATED APPLICATIONS

This application is a continuation-in-part of U.S. patent application Ser. No. 12/187,318, filed Aug. 6, 2008, and also claims the benefit of U.S. Patent Application No. 61/180,187, filed May 21, 2009, both of which are expressly incorporated herein by reference.

BACKGROUND

As an alternative to more invasive types of surgical procedures, many physicians are employing the use of High Intensity Focused Ultrasound (HIFU) as a technique to therapeutically treat internal body tissues. With HIFU, an ultrasound signal of sufficient power (pressure and particle velocity) and time is focused on a target volume of tissue in order to change a state of the tissue by heating and/or by cavitation.

To be effective in treating tissue, the delivered energy of the HIFU signal must be sufficient to cause the desired physical effect. Additionally, the energy must not be so great or uncontrolled as to cause unintended collateral damage to healthy tissues surrounding the target volume. The non-homogenous nature of tissue(s) in the body creates variations in attenuation, propagation velocity, and acoustic impedance that modify the expected acoustic wave propagation and deposition of HIFU energy delivered to a target tissue volume when compared to homogeneous material. The technology disclosed herein is a method and apparatus for dynamically controlling and/or selecting parameters that affect the energy of a HIFU signal and/or the location where the energy is directed so that the desired physical effect in tissue is obtained and collateral damage to surrounding tissue is minimized.

SUMMARY

As indicated above, the technology disclosed herein is a method and apparatus for selecting and/or controlling one or more treatment parameters such as the energy of a HIFU signal delivered by a transducer to a desired location in a patient. The one or more treatment parameters are selected or controlled based on an analysis of harmonic distortion or other changes in a detected signal characteristic that occur as a result of a high amplitude pressure waveform traveling through tissue.

To select a treatment parameter of a HIFU signal that will be used to treat a target tissue site, one or more test signals are delivered to the tissue. Each test signal is a continuous wave (CW) or pulsed mode ultrasound signal that is focused on a target volume in the patient. Signals created by the test signals are received and analyzed to determine a response curve of the tissue that indicates how a signal characteristic changes in response to the one or more test signals. Examples of detected signal characteristics include but are not limited to: energy, power, amplitude, frequency, energy at one or more frequencies or range of frequencies, duration, temperature change, dispersion or acoustic radiation force. The treatment parameter is selected or controlled based on the response curve(s).

In one embodiment, a response curve is compared to find a match against predefined response curves having treatment parameters associated therewith and the treatment parameter(s) of the closest matching response curve is selected.

In another embodiment, a treatment parameter is selected by analyzing a characteristic of the response curve, such as a saturation point or slope and the treatment parameter(s) associated with the characteristic is selected.

In yet another embodiment, a treatment parameter is selected by comparing the response curves to threshold values.

In one embodiment, the response curve is determined by comparing the energy of the received signals created from the test signals in one frequency range to the energy of the received signals in a second frequency range. This comparison is used to calculate K, which is the ratio of the energy in the two frequency ranges. In one embodiment, the energy in the harmonic content of the waveform is compared to the energy in the fundamental frequency. In another embodiment, the energy in a single harmonic, such as the second harmonic, is compared to the energy at the fundamental frequency. In yet another embodiment, the energy in one group of frequencies is compared to the energy in another group of frequencies, of which one may contain the fundamental frequency. In yet another embodiment, the phase difference for the harmonics can be used to calculate K.

The ratio K may be found for a multitude of spatial positions from the transducer. This may be accomplished through windowing of the received signals from the tissue at a specific time and calculating the Fourier transform. The response curve formed by the values of K as a function of spatial location may be compared to a baseline response curve, and the excitation signal may be adjusted to optimize the HIFU energy delivered to the intended target volume.

In one particular embodiment, the disclosed technology relates to a method and apparatus for selecting a power level for a high intensity focused ultrasound (HIFU) signal to be delivered by a HIFU transducer that operates by: transmitting a test signal having a fundamental frequency to a target volume; receiving ultrasound echoes from one or more positions; determining an energy of the received echoes in a first frequency range and an energy of the echo signals in a second frequency range; comparing the energy of the received echoes in the first frequency range and the energy of the echo signals in the second frequency range; and based on the comparison, adjusting one or more characteristics of the HIFU signal to adjust the energy of the HIFU signal delivered by the HIFU transducer.

In still a further embodiment, the method and apparatus operate such that the first frequency range does not include the fundamental frequency of the test signal and the second frequency range does include the fundamental frequency of the test signal.

In still a further embodiment, the method and apparatus operate such that the first frequency range includes one or more harmonics of the fundamental frequency of the test signal.

In still a further embodiment, the method and apparatus operate such that the energy of the received echoes in the first frequency range and the energy of the echoes in the second frequency range are compared by determining a ratio of an energy of the echoes in the first frequency range to an energy of the echoes in the second frequency range.

In yet another embodiment, the method and apparatus operate such that the delivered energy of the HIFU signal is adjusted by determining if the ratio at a selected position is less than a threshold, and if so, adjusting a characteristic of the HIFU signal to increase the delivered energy of the HIFU signal at the selected position.

In yet another embodiment, the method and apparatus operate so that the delivered energy of the HIFU signal is adjusted by determining if the ratio at a selected position is greater than a threshold, and if so, adjusting a characteristic of the HIFU signal to decrease the delivered energy of the HIFU signal at the selected position.

In yet another embodiment, the method and apparatus operate so that the energy of the echoes in the first frequency range and the energy of the echoes in the second frequency range are compared by determining a difference in phase between the echoes in the first frequency range and the second frequency range.

In yet another embodiment, the method and apparatus operate so that the adjustment of one or more characteristics of the HIFU signal is made based on the magnitude of the difference in phase.

In another embodiment, the response curve of the signal characteristic relates a dispersion of an echo signal to variations in test signal power. The dispersion may be detected as an amount of speckle shift toward the HIFU transducer. The one or more treatment parameters are controlled or selected based on the amount of speckle shift detected.

In another embodiment, the response curve of the signal characteristic relates how the energy contained in a received signal at one harmonic or at the fundamental frequency of the test signals varies in response to variations in test signal power.

In another embodiment, the response curve of the signal characteristic relates how a speckle shift due to heating within the tissue changes with changes in test signal power.

In one embodiment, a single test signal at each power level is used to measure the response of the signal characteristic. In another embodiment, two interrogations signals are used for each power level tested. The interrogation signals have the same overall power, but are 180 degrees out of phase. In this case, the signals received from tissue created by the two signals are added together to suppress the fundamental frequency and give a record of the harmonics generated within tissue.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of the disclosed technology will become more readily appreciated as the same become better understood by reference to the following detailed description, when taken in conjunction with the accompanying drawings, wherein:

FIG. 8 shows a graphical representation of K value matrices for different distances and acquisition times;

FIGS. 13A and 13B illustrate different feedback control systems to adjust the energy of a delivered HIFU signal.

DETAILED DESCRIPTION

Although the technology disclosed herein is described with respect to its currently preferred embodiments and the best mode known for practicing the technology, the description is not to be construed as limiting. The disclosure is directed to all new and non-obvious features and aspects of the disclosed embodiments either taken alone or in combination. As discussed above, the technology disclosed herein relates to techniques for adjusting or selecting one or more treatment parameters of a HIFU signal such as the energy of a HIFU signal and/or the location at which the energy is delivered. For the purposes of this application, the energy of a HIFU signal may be characterized by its power, pressure or other related characteristic. Other treatment parameters that can be controlled or selected include the treatment times of the HIFU signals, pulse repetition frequency, pulse duration of the HIFU signals or other parameters that effect the amount or rate at which energy is deposited at a tissue treatment site.

As will be described in further detail below, the one or more treatment parameters of the HIFU signals that are used to treat a tissue site are controlled or selected based on an analysis of how the signal characteristics of received signals vary in response to one or more test signals. In a currently preferred embodiment, the test signals are one or more HIFU signals. However, the test signals could be any type of ultrasound signal including non-focused or imaging ultrasound signals. The same transducer may be used to deliver both the therapeutic HIFU signals and the test signals or different ultrasound transducers could be used.

In one embodiment, to select the value of a treatment parameter, a number of test signals at different power levels are transmitted into the tissue. The test signals may be transmitted to the same tissue region as the target treatment site or the test signals may be transmitted into tissue into tissue that is nearby the target treatment site.

As the power level of the test signals increase, the transmitted test signals become increasingly non-linear in the tissue in the focal zone of the ultrasound transducer. The non-linearity creates a corresponding response curve of a signal characteristic that can be detected and used to select the appropriate treatment parameter. In one embodiment, the response curve is analyzed for a power level of a test signal that causes the detected signal characteristic to saturate. The saturation power level is used as a basis for selecting the treatment parameter.

The treatment parameter may be selected for each tissue site to be treated. Alternatively, the selected treatment parameter may be used to treat several different areas or cross-sections of the tissue site to be treated.

Figure 1:
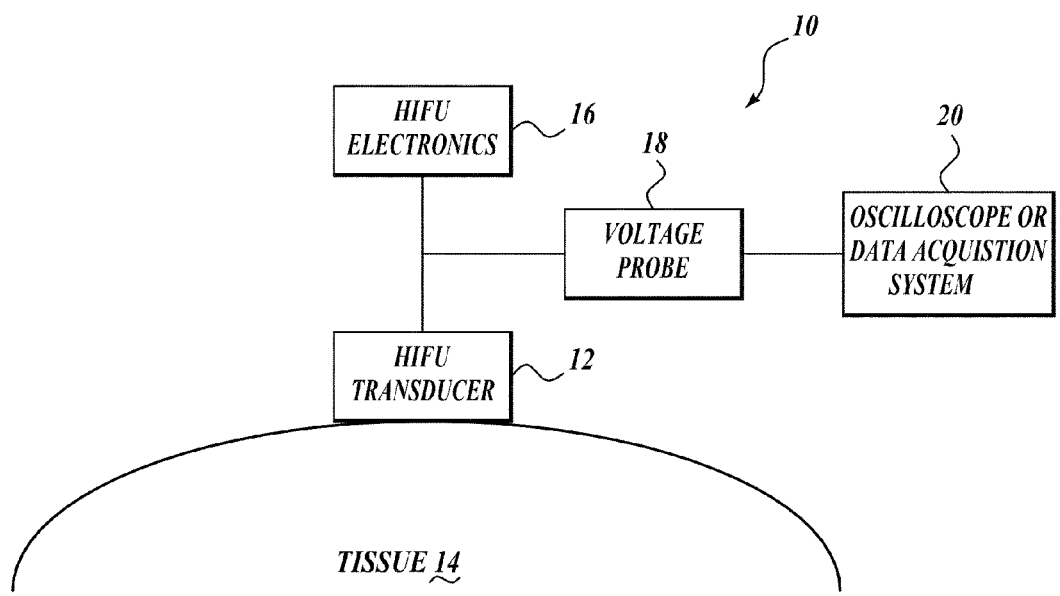
FIG. 1 illustrates a basic system for controlling the energy of a delivered HIFU signal, in accordance with an embodiment of the disclosed technology.

FIG. 1 shows a diagram of a system for selecting a treatment parameter such as the energy of a HIFU signal for use in treating a tissue site in accordance with an embodiment of the disclosed technology. The system 10 includes a HIFU transducer 12 that delivers a HIFU signal to tissue 14 and HIFU electronics 16 that excites the transducer 12. A voltage probe 18 detects an electrical signal at the HIFU transducer 12. The system further includes an oscilloscope or other data acquisition system 20. In this case, an excitation signal from the HIFU electronics 16 stimulates the HIFU transducer 12 such that a high energy ultrasound signal is transmitted to the intended target in tissue 14. The energy in the HIFU signal is scattered, reflected, transmitted and absorbed as it propagates within the tissue. The absorbed energy is converted to heat and causes the temperature of the tissue to rise. The amount of energy absorbed depends on the pressure amplitude and frequency as well as the tissue characteristics. Typically, a HIFU device is designed such that the greatest pressure and absorption occur at the focal point of the device in the tissue. Energy of the signal that is not absorbed is either transmitted to deeper tissues or reflected and scattered. In one embodiment of the disclosed technology, it is the reflected and scattered energy (ultrasound echoes) that can be detected and analyzed for harmonic distortion. Some of this scattered acoustic energy is detected by the HIFU transducer 12 and converted into an electrical signal. The electrical signal is sensed using the voltage probe 18 and displayed/acquired on the oscilloscope or other data acquisition system 20.

Figure 2A:
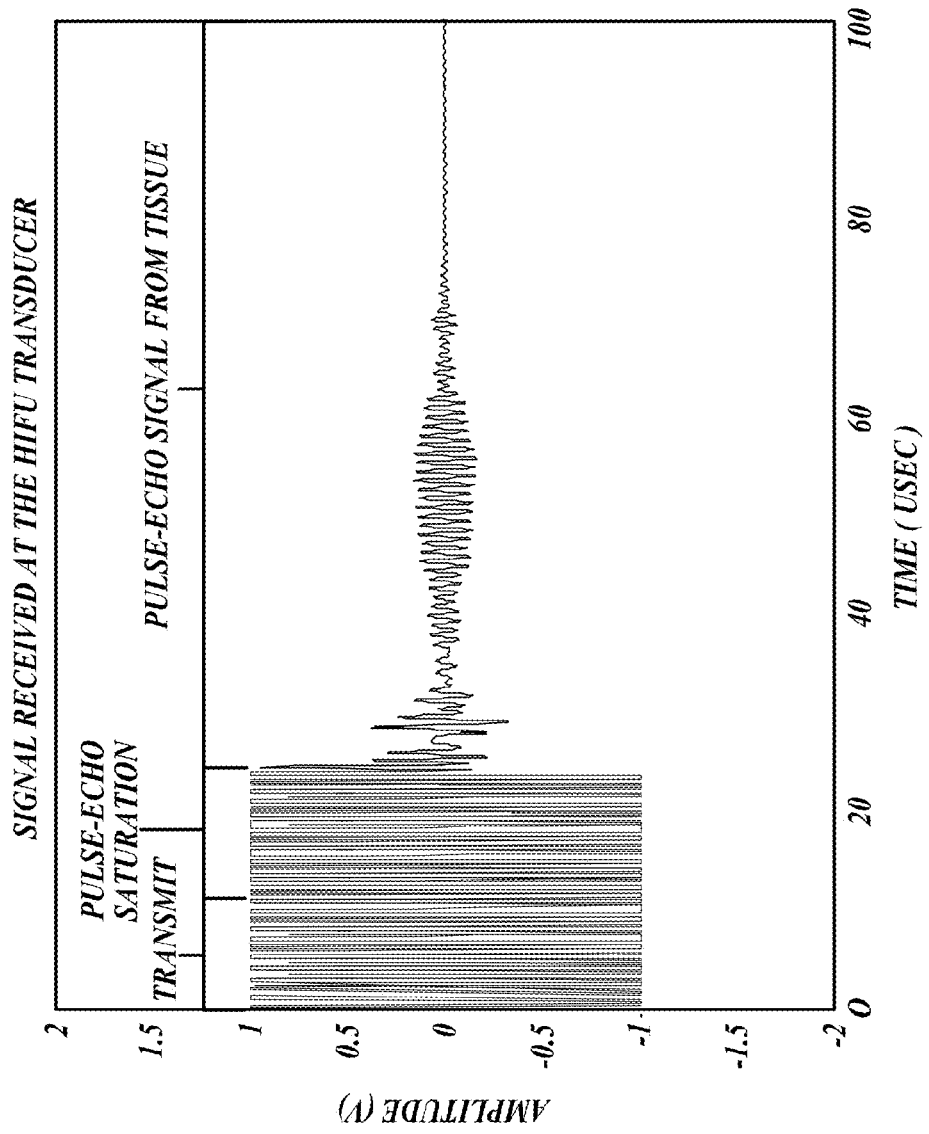
FIG. 2A shows a received echo as a function of time.
Figure 2B:
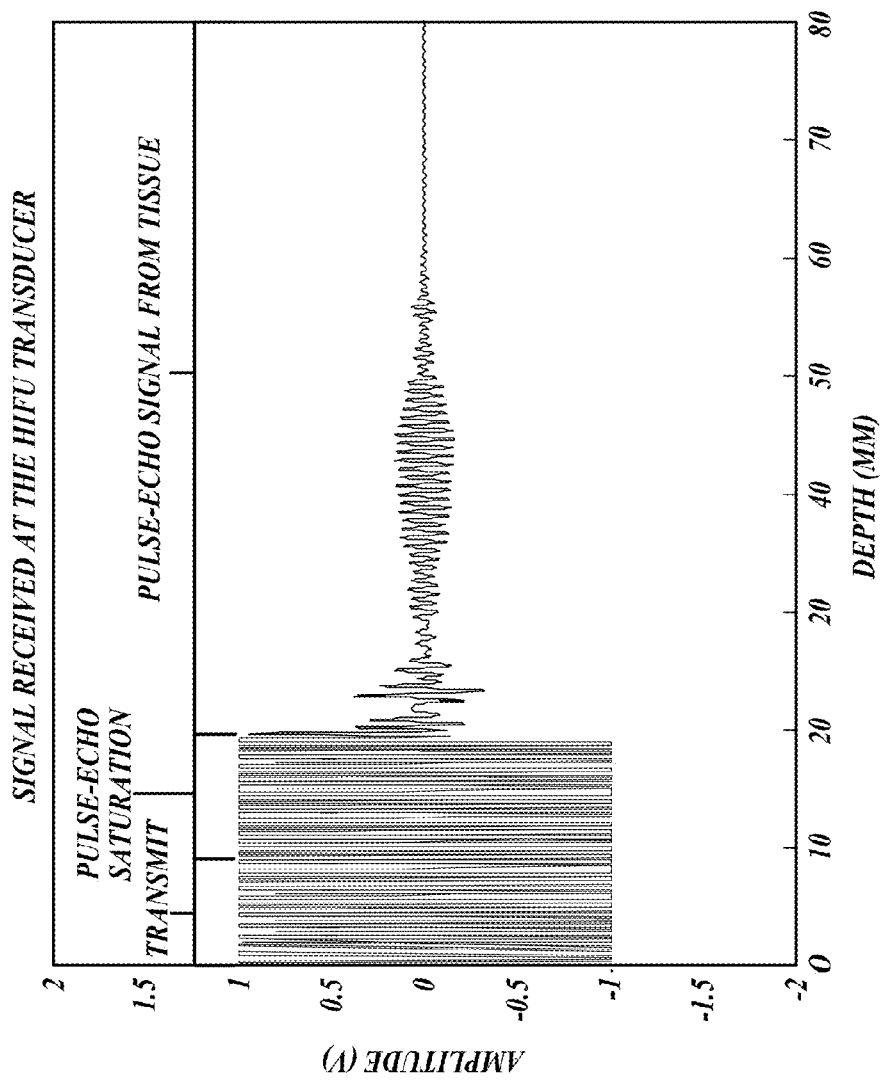
FIG. 2B shows a received echo as a function of distance.

FIG. 2A shows a representative signal captured at the data acquisition system 20 with three regions identified, namely transmit, pulse-echo saturation, and pulse-echo signal. For this example, the focal depth is 35 mm for the HIFU transducer. If it is assumed that acquisition starts immediately when transmit begins, then the first detected signal will contain mostly information from the transmit pulse (transmit region). After transmit ends, it is expected that some of the first few echoes may cause clipping in the detection system (pulse-echo saturation). The issues with pulse-echo saturation may be mitigated by properly designing the detection circuit to ensure satisfactory dynamic range and bandwidth (e.g. time-gain control). After the initial large amplitude echoes have been received, the echoes from the tissue may be detected without any additional distortion added from the detection system (pulse-echo signal). Since in the embodiment shown, the HIFU transducer and detection transducer are the same, the time axis also represents depth through knowledge of the propagation velocity in the tissue as shown in FIG. 2B.

Figure 3:
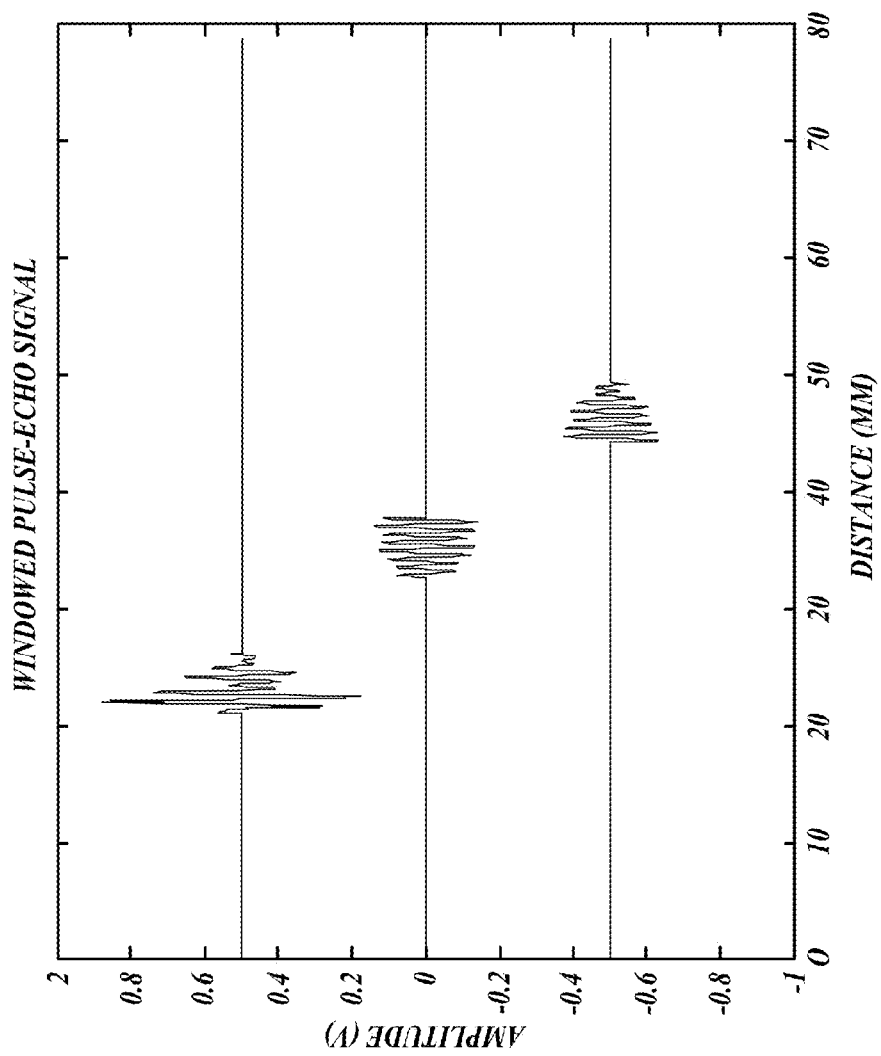
FIG. 3 shows windowed sections of a received echo at three different distances.
Figure 4:
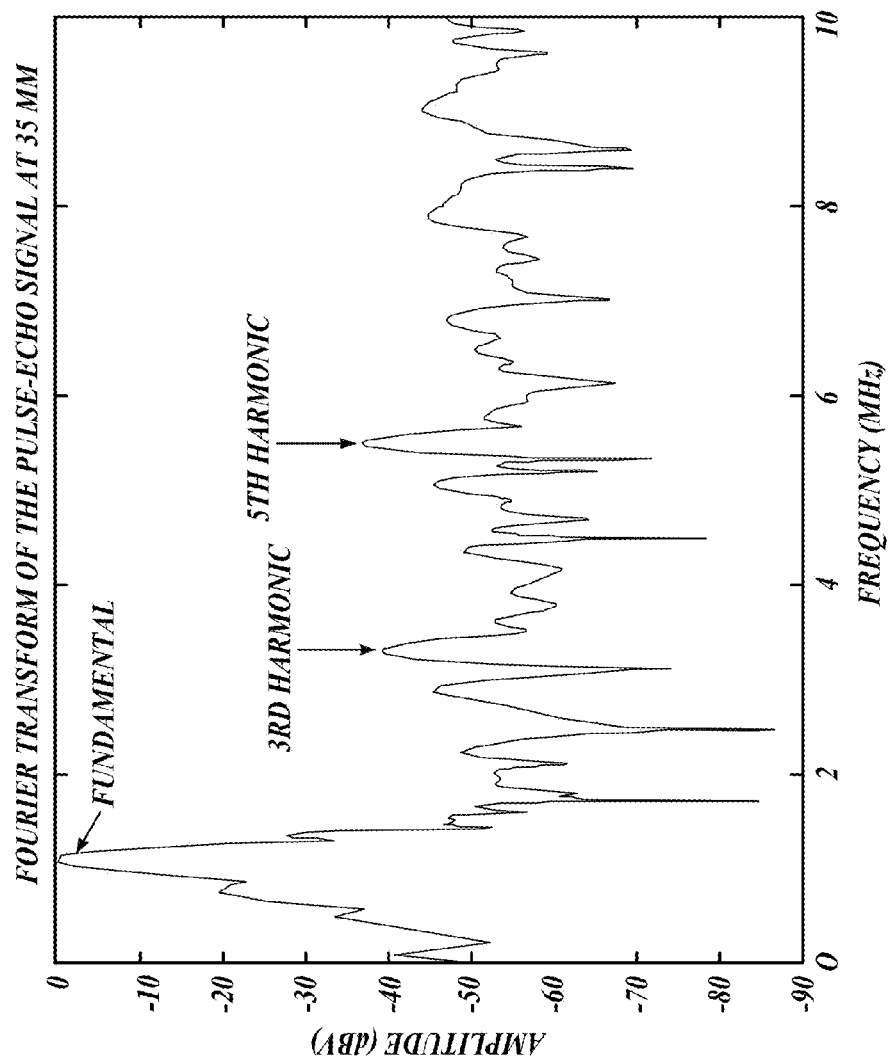
FIG. 4 shows the frequency spectrum of a windowed echo (distance of 35 mm) with the fundamental, 3rd and 5th harmonics identified.
Figure 5:
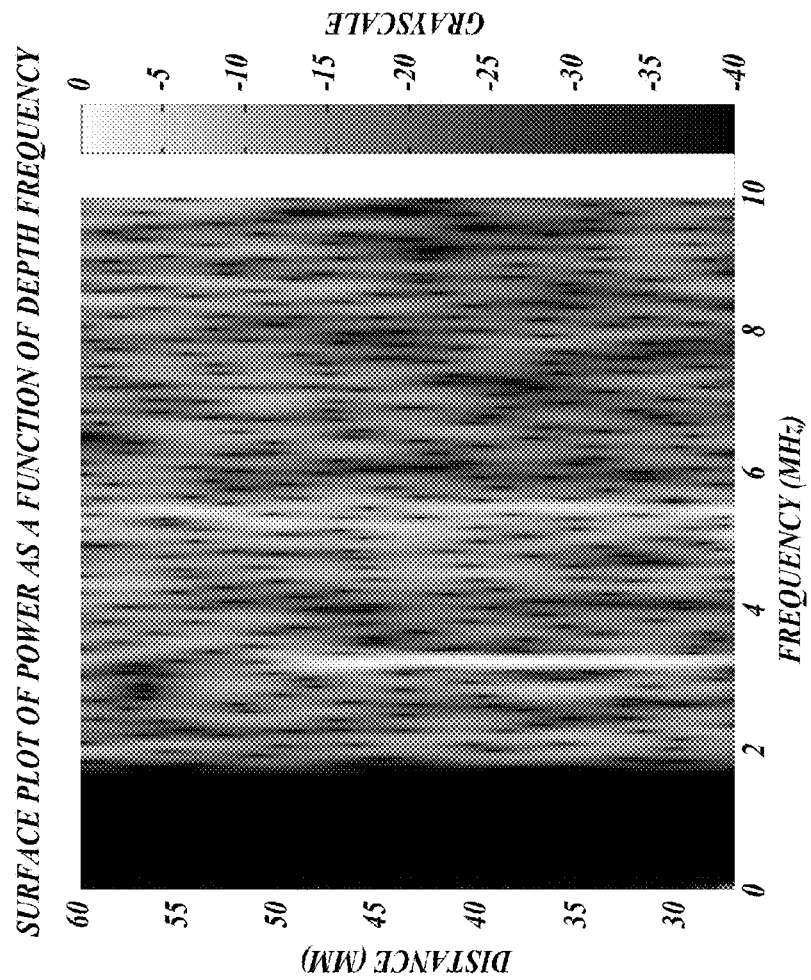
FIG. 5 shows a surface plot of the power in decibels as a function of frequency and distance mapped to a grayscale.

The energy of the echo signals as a function of frequency may be computed at different depths or spatial locations. In one case, the received echo signal is multiplied by a windowing function centered at a specific depth and the Fourier transform operator is applied. In the example shown in FIG. 3, echo signals are isolated at depths centered at 25, 35 and 45 mm with a rectangular function which is 5 mm in width. It is expected that the window width and amplitude will be adjusted to optimize the frequency representation of the echo signal. A Fourier transform of the echo signals at each depth signal is calculated to determine the energy of the echo signals as a function of frequency. FIG. 4 shows the frequency spectrum for the signal windowed at 35 mm. In this case, the fundamental frequency, $3^{rd}$ harmonic, and $5^{th}$ harmonic are identified. The even harmonics are typically not as easy to detect due to therapy transducer limitations. Although only three depths are shown in FIG. 3, the window function can run along the entire length of the pulse-echo signal or vector. In this case, a matrix of data is computed such that one axis is depth and the other axis is frequency. FIG. 5 shows a three dimensional surface plot in grayscale of a continuous analysis along the depth dimension. In this representation, the fundamental frequency of 1.1 MHz has been removed using a digital filter, which highlights the harmonics seen at 3.3 MHz and 5.5 MHz.

The Fourier transform determines the energy that occurs in a number of frequency bins. Therefore, the energy in a particular frequency bin may be compared to the energy in other frequency bins or the energy over multiple frequency bins may be summed and compared. For example, frequencies around the fundamental frequency (e.g. bandwidth) may be a better representation of the power. EQUATIONS 1A and 1B show two different cases for calculating a ratio K, of the energy as represented by the power at two different frequencies or in different frequency ranges.

As with many signal processing schemes, signal conditioning may be required to detect and properly represent the energy of the echo signals at the various frequencies. For example, the sensitivity of the detection transducer or attenuation as a function of frequency and depth may need to be introduced to fully appreciate differences in the energy at the various frequencies in tissue.

$$K_{f_1 f_0}(r) = \frac{P(f_1, r)}{P(f_0, r)} \quad (1A)$$

$$K_{f_1 f_0}(r) = \frac{\sum_{f=f_1-\Delta f}^{f_1+\Delta f} P(f, r)}{\sum_{f=f_0-\Delta f}^{f_0+\Delta f} P(f, r)} \quad (1B)$$

FIG. 5 shows that the K values can be calculated as a function of spatial position or depth; therefore, K is a function of r or spatial distance. It is important to note that the calculation may include one frequency or multiple frequencies. For example, the K value may represent the energy in the harmonics compared to the energy in the fundamental.

Figure 6:
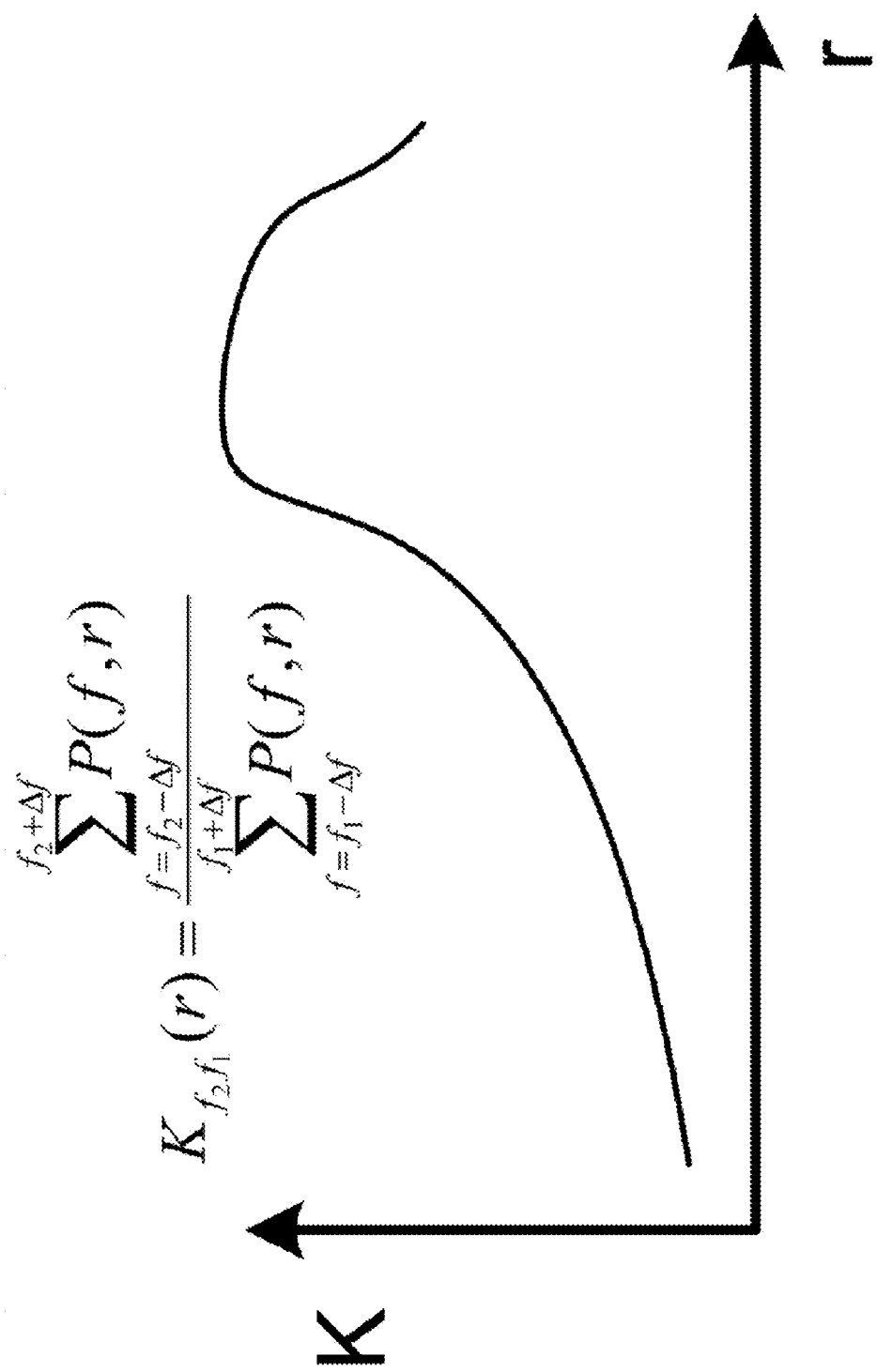
FIG. 6 shows an expected K value curve as a function of distance 'r'.

FIG. 6 shows an example of how the K values are expected to vary as a function of depth. In this example, the energy around the fundamental is compared to the energy in the harmonics. As can be seen, the ratio K has a maximum at or adjacent the focal point of the HIFU signal and then decreases with increasing distance away from the transducer.

Figure 7A:
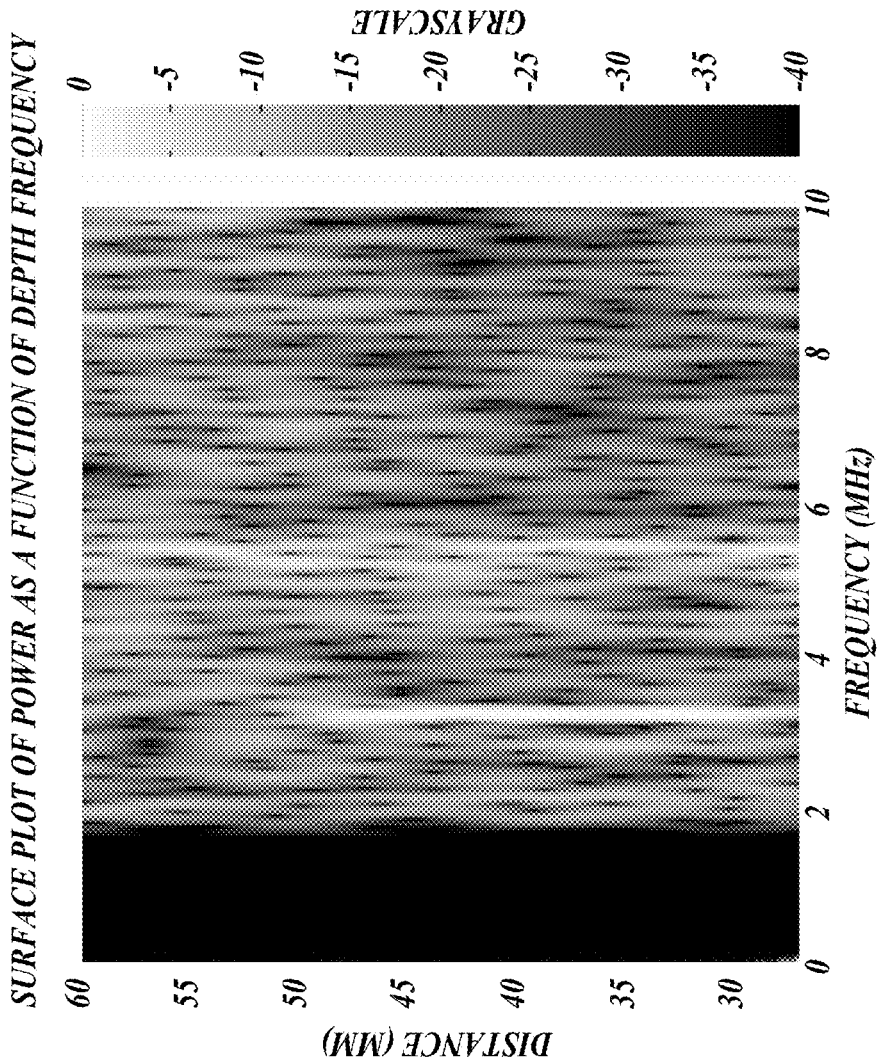
FIGS. 7A-7C show a surface plot of the power in decibels as a function of frequency and depth taken at three different times, t0, t1 and t2.
Figure 7B:
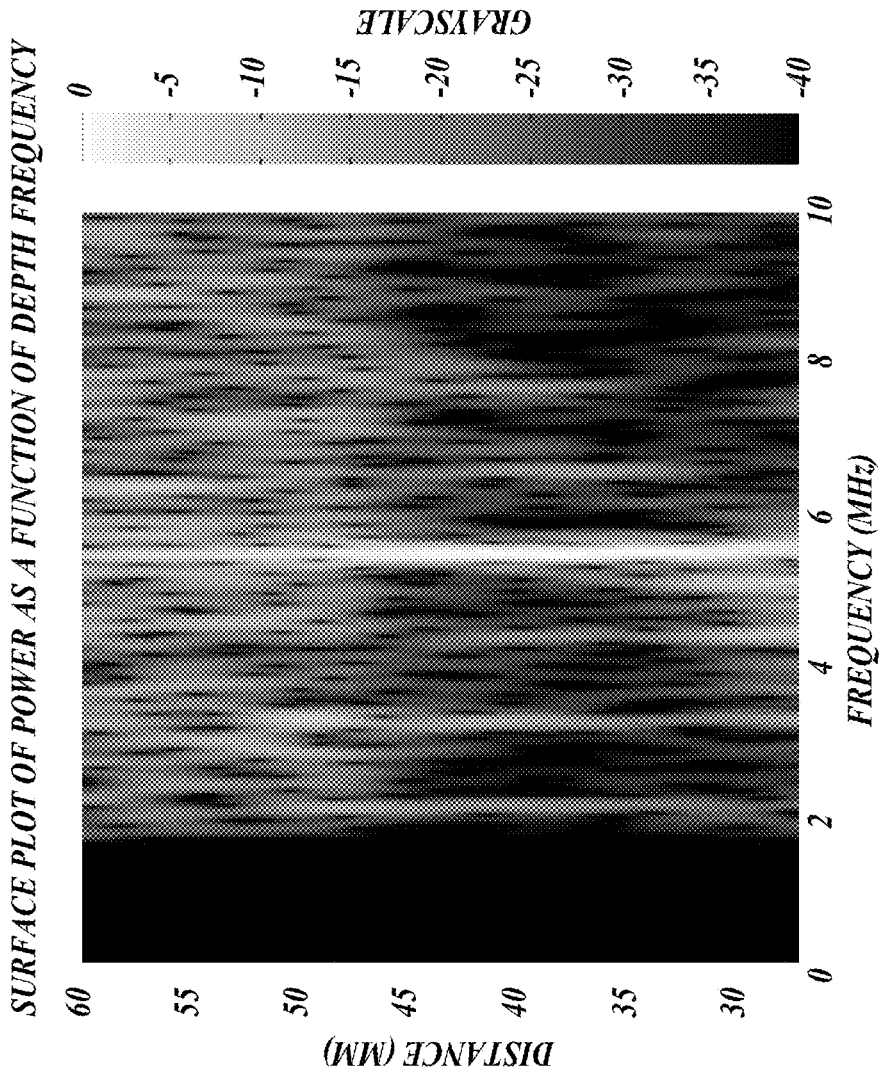
Figure 7C:
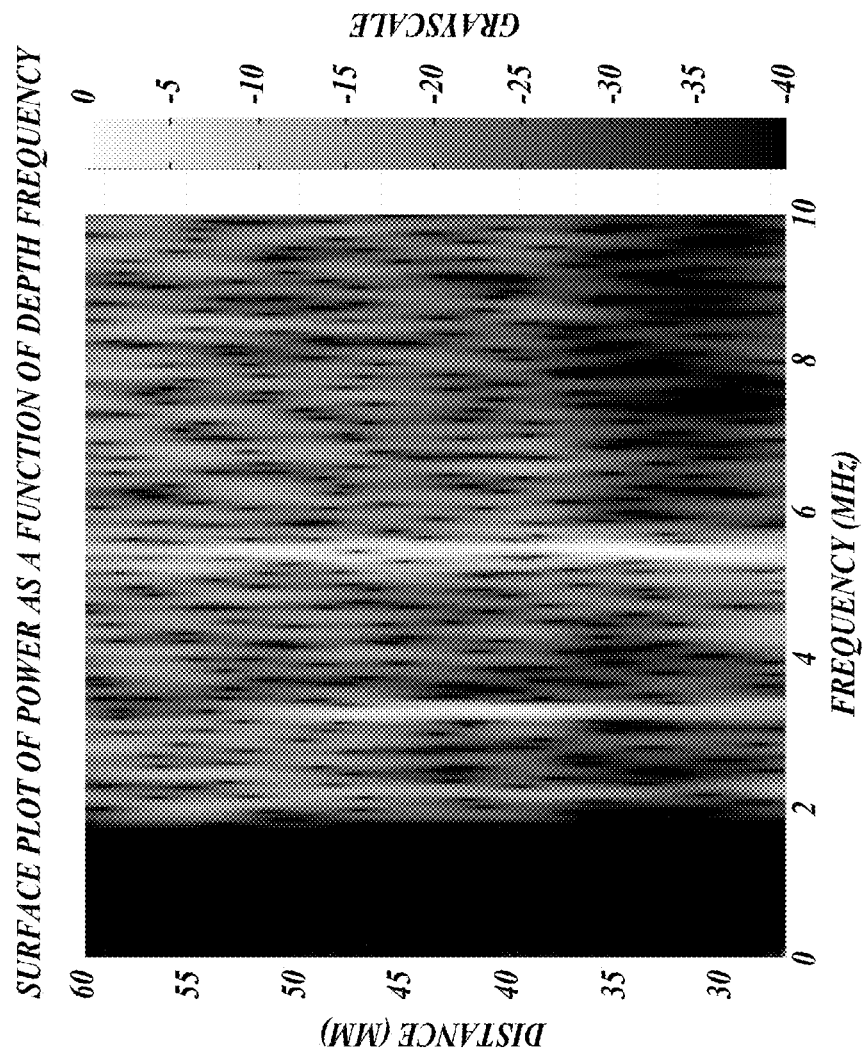

As described, it is possible to map the energy ratio as a function of frequency and spatial location for an echo. If the excitation level at the transducer is modified, then it is also possible to compare K values for different HIFU transducer pressures. The echoes are also available at different sampling intervals (pulse repetition interval). For example, if a pulse mode HIFU excitation is used, then the echo may be detected and analyzed between the excitation signals. This allows the K values to be compared for multiple excitation levels and/or multiple times. FIGS. 7A-7C show multiple surface plots that have been acquired from different echoes at times t0, t1 and t2. This may be due to variation in excitation level or just processing between excitation times. The frequency spectrum at each spatial location is calculated, and then K is calculated.

Figure 8:
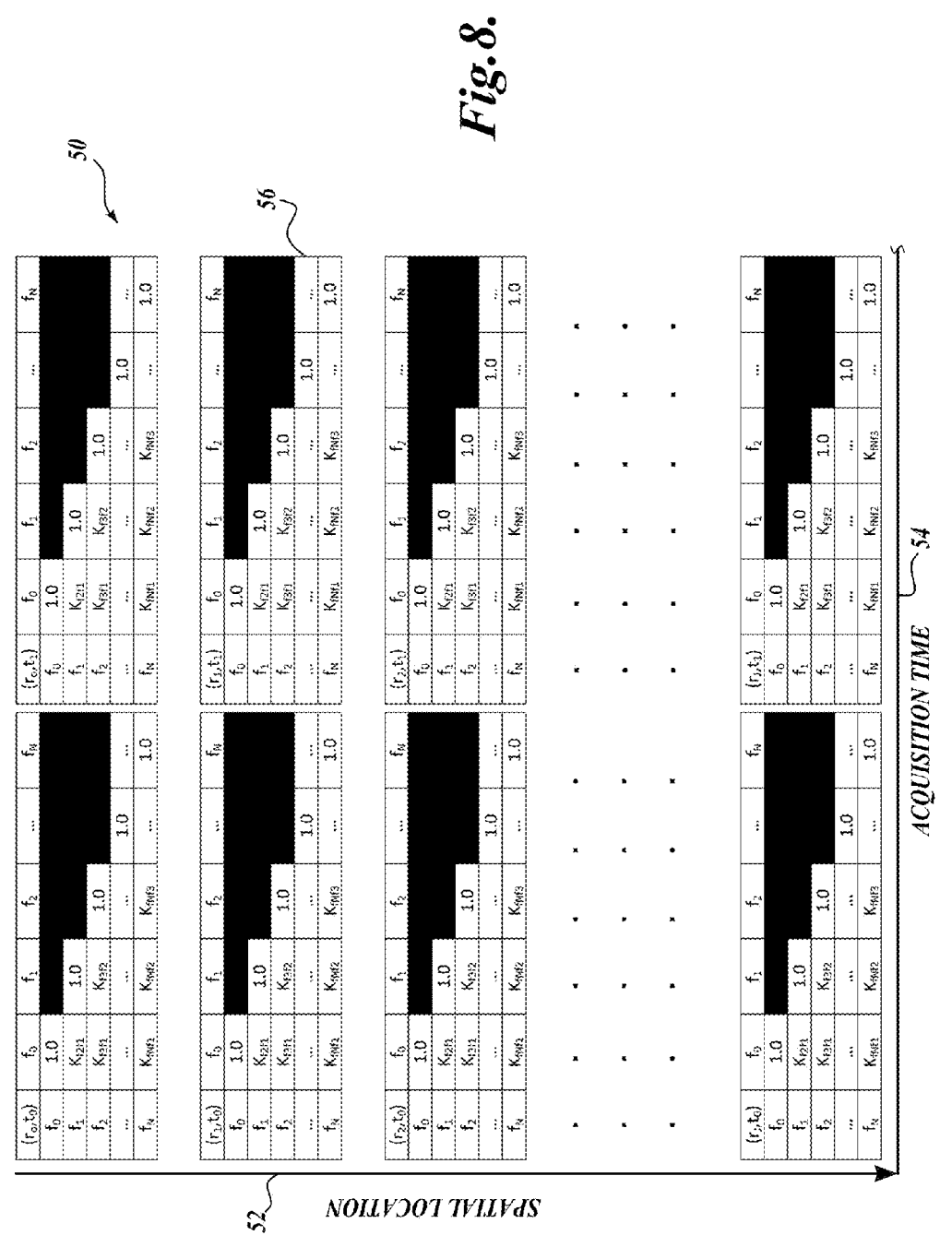

FIG. 8 shows a representative format for storing K data in a computer memory. In one embodiment, the data is stored in a table 50 where one axis 52 is spatial location (depth) and another axis 54 is acquisition time. Each entry for a particular depth and time contains a matrix, e.g., 56, wherein the power ratio between two frequencies is calculated and stored. In this representation, $K_{f_2/f_0}$ is the power ratio in the third harmonic to the fundamental frequency. $K_{f_2/f_1}$ is the power ratio in the third harmonic to the second harmonic. Since K is just a ratio of the power in two frequencies, $K_{f_2/f_1}$ is simply the multiplicative inverse of $K_{f_1/f_2}$. If it is necessary to compare the power in the fundamental to all harmonics, then essentially the column needs to be summed as set forth in EQUATION 2.

$$K_{total}(r_0,t_0) = K_{f_1/f_0}(r_0,t_0) + K_{f_2/f_0}(r_0,t_0) + K_{f_3/f_0}(r_0,t_0) + \ldots + K_{f_N/f_0}(r_0,t_0) \quad (2)$$

FIG. 8 also shows that the K values may be calculated at different excitation times t0, t1, t2, etc. By comparing the K values at these times (note: the excitation may vary at these different times) between each other or to a baseline, the approximate location of the focus may be determined as well as an estimate of the energy of the HIFU signal delivered to the tissue.

The values of K can be used to select a treatment parameter for the HIFU signals to be used in treating a tissue site by analyzing the K curve determined for the tissue. As indicated above, the system transmits one or more test signals into the patient and detects signals created by the test signals. The ratio, K, of the energy detected in different frequency bands versus depth can be used to create a K curve. The K curve of the detected signals can be compared against known K curves for which treatment parameters have already been determined. For example, breast tissue may be associated with a K curve having a first set of one or more treatment parameters. Fibroid tissue may be associated with another K curve having different treatment parameters. In one embodiment, a processor compares the K curve for the detected signals with a library of K curves to determine the closest match and selects the treatment parameters associated for the closest match.

In another embodiment, one or more individual points on a K curve for the detected signals can be compared with a predetermined baseline K curve. The value for the treatment parameter can be adjusted based on the comparison. For example, if the characteristic curve formed by K as a function of spatial location for the detected signals shows significantly higher ratios than the baseline curve, then the output energy (pressure) may be reduced. Similarly, if the characteristic curve formed by K as a function of spatial location for the detected signals shows significantly lower ratios (or flatter) than the baseline curve, then the output energy may be increased.

It is also possible to show harmonic saturation (maximum value for the ratio K) by graphing the K values as a function of the excitation amplitude for a particular depth. In this case, a number of test HIFU signals are transmitted at different power levels and the K values for the detected signals are computed. A curve or plot of the change in K versus changes in HIFU power for a particular depth are computed. The curve or plot can then be compared against known plots having treatment parameters associated with them. Alternatively, the K curve can be compared with a baseline K curve and the treatment parameters selected.

In one embodiment, one or more points on the K curve for the detected signals are used to select the treatment parameters. In one embodiment, the K curve can be searched for a HIFU power level that causes the value of K to saturate. The treatment parameters of the HIFU signals used to treat a tissue sample can therefore be selected based on the HIFU power which causes the K value to saturate. For example, if the HIFU power that causes the value of K to saturate is 1500 watts, then the treatment parameters associated with a 1500 watt level can be used to treat the tissue. In some cases it may be useful to use the same power to treat the tissue as the power that causes the value of K to saturate. In other cases, other power levels (greater or lessor) could be used.

In yet another embodiment, other characteristics of the K curve for the detected signals can be used to select the treatment parameters. For example, the slope of the K curve can be compared with slopes of K curves having treatment parameters associated with them or the slope of the K curve for the detected signals can be compared with a baseline and the treatment parameters adjusted accordingly.

If the excitation level is constant during the treatment, the energy level of the harmonics and their location may suggest the amount of heating occurring throughout the tissue. This would help determine a limit to the amount of energy delivered to the intended target.

It should be also noted that although the power spectrum has been calculated at different depth and acquisition times, the phase may also be used to determine the amount of heating in tissue.

Since the K-value may be derived by the taking the Fourier transform of the echo signals, the power (energy per unit time) falling within each frequency bin as well as the phase is available for computation. The magnitude and phase in a particular frequency bin may be expressed in the following equation:

$$H(f_1) = A(f_1) * e^{-j2\pi\phi(f_1)} \quad (3)$$

where $A(f_1)$ is the amplitude of the signal at frequency $f_1$ (the power is simply the square of A) and $\phi(f_1)$ is the phase of the signal at frequency $f_1$. Therefore, the phase difference between two frequency bins may be computed by taking the ratio of Equation 3 with the magnitude normalized to 1:

$$\epsilon_{f_1 f_0} = \frac{e^{-j2\pi\varphi(f_1)}}{e^{-j2\pi\varphi(f_0)}} \quad (4)$$

Equation 4 may be rewritten as $$\epsilon_{f_1 f_0} = e^{-j2\pi(\phi(f_1) - \phi(f_0))} \quad (5)$$

The argument in Equation 5 is the phase difference between the two signals. The phase difference as a function of depth at different excitation levels may also be used as a relative measure of energy in different frequencies or frequency bands, which in turn may be used to dynamically control or select a treatment parameter of a HIFU signal. For example, the magnitude of the phrase difference can be compared to a threshold previously known to relate the phase difference to delivered energy in the tissue. One or more characteristics of the HIFU signal can then be adjusted in accordance with the comparison.

Figure 9:
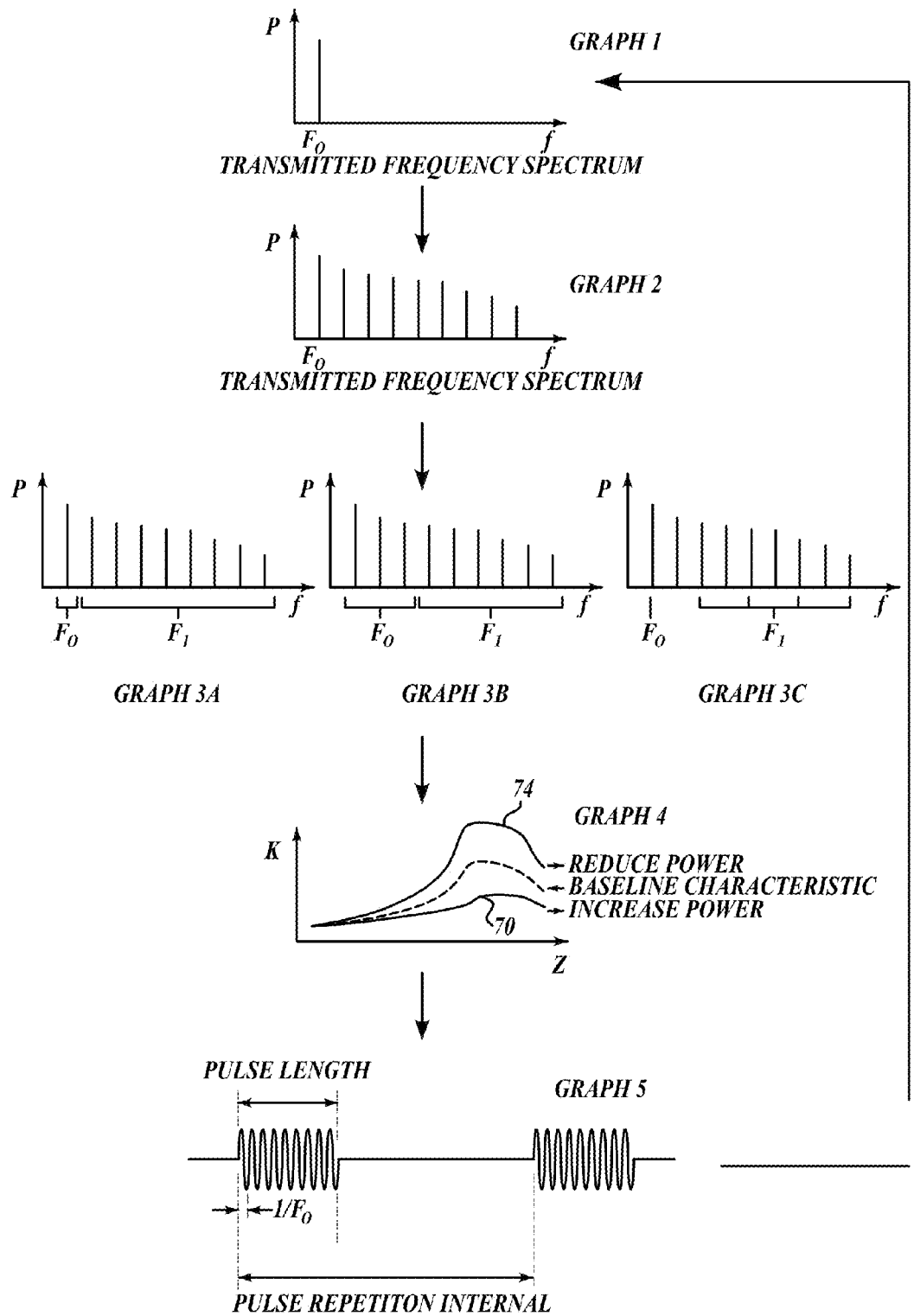
FIG. 9 shows a graphical representation of the steps performed to obtain K value curves and change the energy/power of a delivered HIFU signal in accordance with an embodiment of the disclosed technology.

FIG. 9 shows a summary of the basic steps to acquire the K values in accordance with one embodiment of the disclosed technology. First, the HIFU transducer is excited with a single frequency ($f_o$) as shown in graph 1. The HIFU signal may be a continuous wave (CW) or a pulsed sinusoid with a fundamental frequency $f_0$. In the case of CW, the pulse repetition interval is equal to the pulse length. As shown in graph 1, the HIFU excitation signal generated at the HIFU transducer probe has a signature spectrum where the energy of the frequency components that are different from the fundamental frequency of the HIFU signal, such as the harmonics, $f_1, f_2, f_3$, etc., are negligible compared with the energy of the fundamental frequency $f_0$. The high pressures created from the transmitted HIFU signal converts the energy at the fundamental to harmonics and in the tissue (graph 2). In particular, the energy of the signal at frequencies that are different from the fundamental frequency $f_0$ the HIFU signal (such as the frequency of one or more of the harmonics $f_1, f_2, f_3$, etc.) changes in comparison to the energy of the signal at the fundamental frequency $f_0$ as shown in graph 2. K values are calculated by combining the energies at these various frequencies as shown in graphs 3a, b and c. For example, the energy in one or more of the harmonics may be compared to the fundamental frequency. The energy in several lower order harmonics and the fundamental may be compared to that of the high frequency harmonics. Alternatively, the energy in the fundamental may only be compared to that of the higher order harmonics. These graphs by no means exhaust the possibilities of combining and comparing the energies at the various frequencies. As will be appreciated by those skilled in the art, the value of K may vary depending on the range of frequencies or particular harmonics used in computing the numerator and denominator.

Graph 4 shows that the K values may be graphed as a function of position. The ratio K may vary with the depth in the tissue as well as with different levels of transmit excitations. In one embodiment, the ratio K is expected to be a non-linear curve that increases with increasing depth in the tissue, but tends to reach a maximum (or saturate) at approximately the depth of the focal point of the HIFU signal. If K values are calculated after each transmit pulse (graph 5), then multiple K value curves may be generated as shown in graph 4.

Figure 10A:
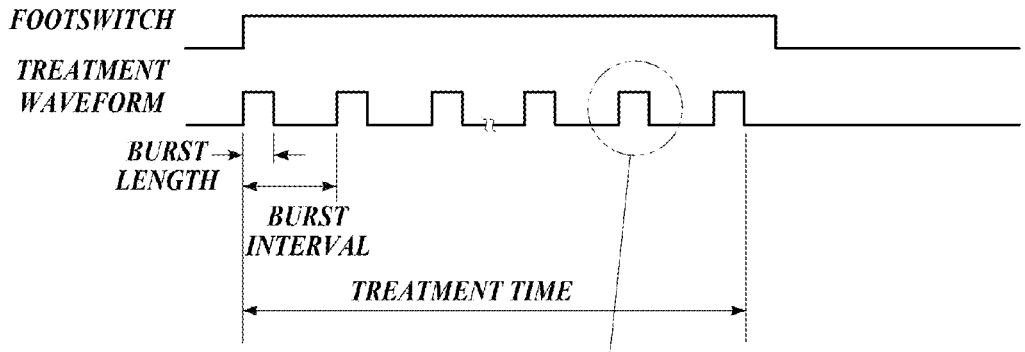
FIGS. 10A-10C illustrate the differences between burst length, burst interval, pulse length, and pulse rate interval of a pulsed HIFU signal.
Figure 10B:
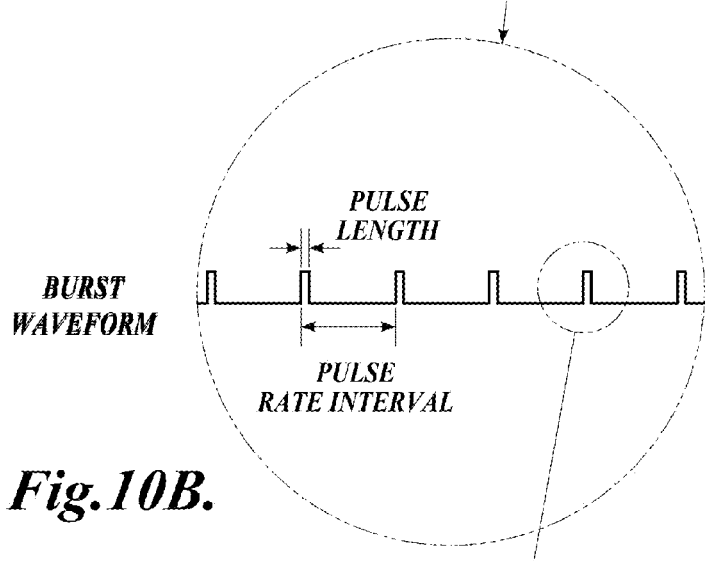
Figure 10C:
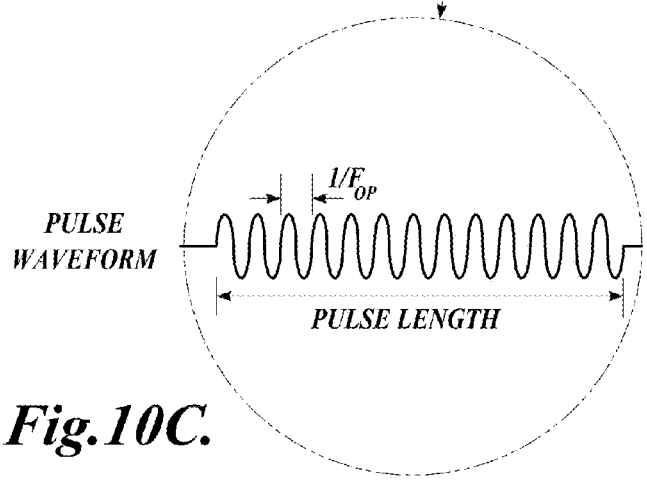

Graph 5 shows that the frequency of the transmit pulses may occur at the pulse repetition interval. FIGS. 10A-10C illustrate a pulse length and a pulse repetition interval in a burst. Many pulse lengths make up a burst. Each burst has a defined burst length, and the time between the start of each burst is the burst interval as shown in FIG. 10A. Each HIFU burst includes a number of HIFU pulses having a pulse length, where the time between the start of each pulse is the pulse rate interval as shown in FIG. 10B. The total time of the transmit excitation is the pulse length as shown in FIG. 10C. Each HIFU pulse is a sinusoidal waveform having a fundamental frequency $f_0$.

Returning to FIG. 9, a first curve 70 in graph 4 illustrates the ratio K for a first delivered energy level of the HIFU signal and a second curve 74 illustrates the ratio of K for a higher level of energy. By observing the changes in the K values as a function of depth, time, or transmit excitation, then a relative measure of the energy deposited spatially may be approximated.

The energy of the HIFU signal can be modified by increasing or decreasing any of the burst length, the burst interval, the pulse length, the pulse rate interval, or other characteristics such as the pulse amplitude. In one embodiment, the HIFU treatment system automatically varies the acoustic output energy or power as a function of both the characteristic K curve relative to the baseline characteristic curve and whether the device is within an acceptable range for the values of K. An acceptable range for K may have an upper limit for prefocal and focal values of K, based on safety levels. Other treatment parameters such as treatment time or pulse repetition frequency of the HIFU signals can be selected in a similar manner.

Figure 11:
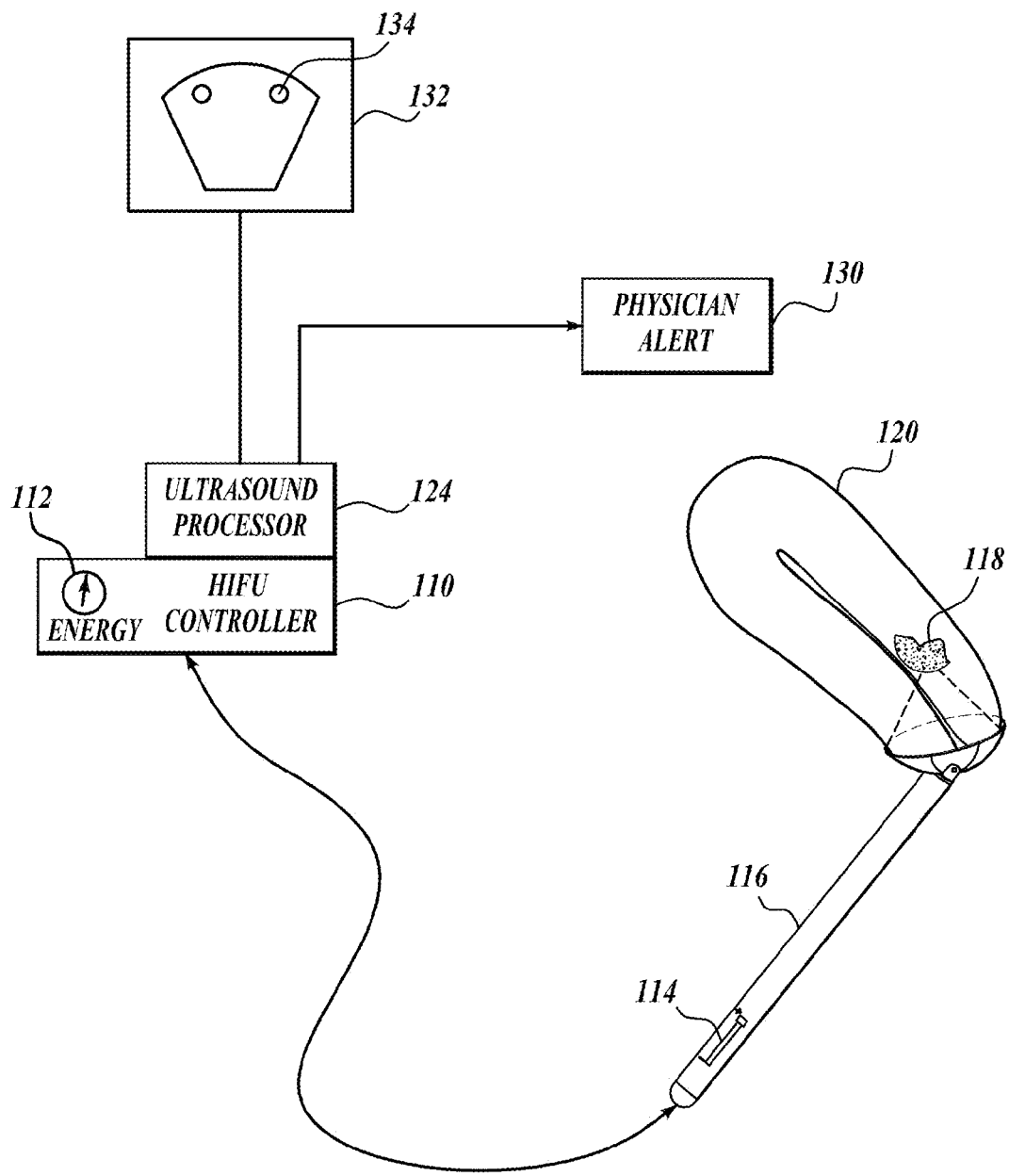
FIG. 11 illustrates an embodiment of a HIFU treatment system in which the disclosed technology can be implemented.

FIGS. 1 through 10 illustrate an embodiment of the disclosed technology starting with a simple block diagram. As one trained in the art will appreciate, there are other versions of this technology that generate similar benefits. FIG. 11 is another block diagram of a HIFU treatment system for implementing the technology disclosed herein. In the embodiment, a HIFU controller 110 delivers electronic driving signals to an external or internal transducer probe 116 that in turn converts the driving signals into acoustic HIFU signals. In FIG. 11, the HIFU transducer probe 116 is shown in a wand-like apparatus. It is important to note that the HIFU transducer many have a plurality of elements in multiple dimensions that are mechanically or electronically steered to properly direct the ultrasound signal to the intended target. For example, the HIFU signals may be directed to a focal zone that is aimed at a target volume 118 through electronic or mechanical means. The target volume 118 may include all or a portion of a fibroid in a uterus 120. The HIFU signals create corresponding echo signals from tissue that are intercepted by the acoustic propagation. In most cases, the HIFU signal energy is concentrated on an axis that is located between the transducer probe 116 and the focal zone.

The echo signals are received by the transducer probe 116, converted into an electronic form and supplied to the HIFU controller 110. The detection of the echo signals may take place in the HIFU transducer or another specially designed device contained within the transducer probe 116. Furthermore, the detection device may be in a separate holder not contained within the transducer probe 116.

As previously described, the K values from the echo signals are calculated (FIG. 9), analyzed, and used to control or select one or more treatment parameters. An ultrasound processor 124 that is connected to or incorporated within the HIFU controller 110 analyzes the received echo signals and computes the K values. Based on the analysis, one or more treatment parameters or characteristics of the HIFU excitation signal (e.g., peak power, average power, pulse duration, pulse repetition interval, etc.) are automatically or semi-automatically adjusted by the ultrasound processor 124. In some cases, the operator may be alerted via an audible, visible, or tactile alert 130 to manually adjust one of the device parameters through a control on the device (e.g., main console control 112, applicator, footswitch). A safety mechanism to ensure treatment does not continue without proper feedback signals may also be employed. In some instances, the system may also include ultrasound imaging capabilities that produce images of the tissue on a video display 132. The images may be obtained with a separate or integrated imaging ultrasound transducer. These images may be used to confirm proper adjustment of the HIFU excitation characteristics.

To estimate how much of the incident HIFU energy is being absorbed by the tissue at various positions at or adjacent to the focal point of the HIFU signal, the value of the ratio K is determined from the echo signals received from a given point in the tissue. In one embodiment, the ratio is compared to a desired value of K that was determined from prior testing. The value of the ratio K for the detected signals can therefore be used as a feedback signal to adjust one or more characteristics of the HIFU signal to affect absorption and hence HIFU effects on tissue at a given point. Detection of saturation (acoustic shock waves) or the slope of the increase in the K value as a function of the transmit excitation may also be used as feedback mechanisms to adjust one or more characteristics of the HIFU signal rather than depending on prior testing.

In one embodiment, if the determined value of K for detected signals is below a threshold value for a particular position in the patient, then a signal characteristic such as the amplitude, peak or average power, duty cycle, pulse repetition rate, or other characteristic of the delivered HIFU signals can be electronically or manually increased to increase the ratio K at that position. Conversely, if the determined value of K is above a threshold, then one or more of the amplitude, power, duty cycle, pulse repetition rate, or other characteristic of the HIFU signal can be decreased to decrease the value of K. Different threshold values of K may be used to analyze echo signals received from within the target volume and outside that target volume in the body.

Figure 12A:
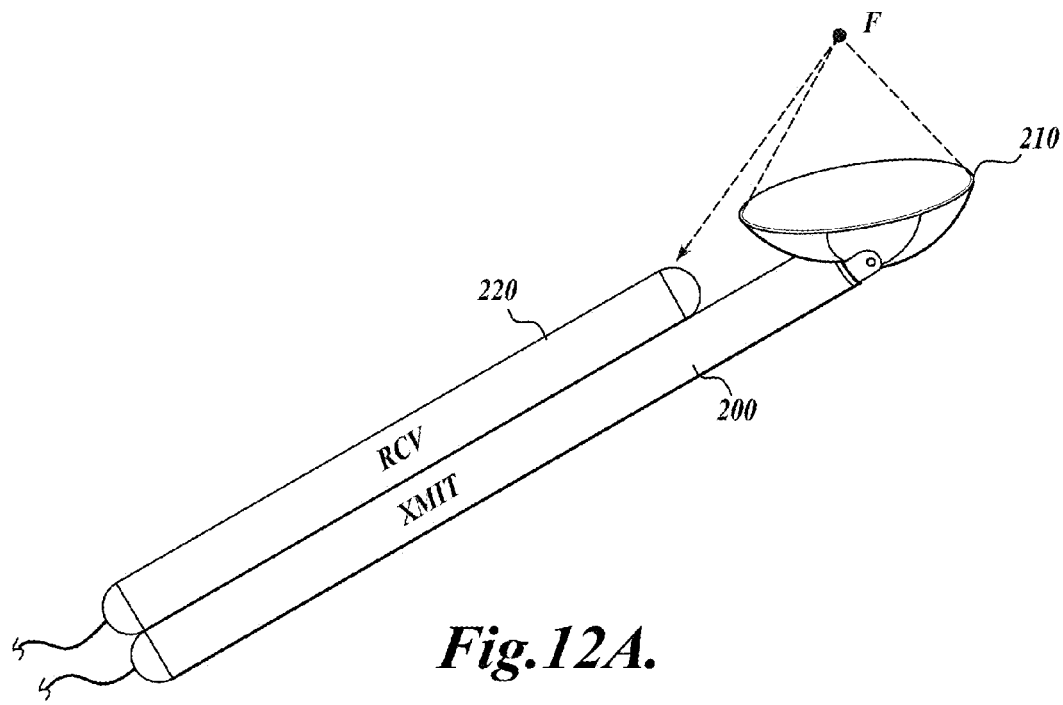
FIGS. 12A and 12B illustrate different types of transducer probes that transmit HIFU signals and receive echo signals from the patient.
Figure 12B:
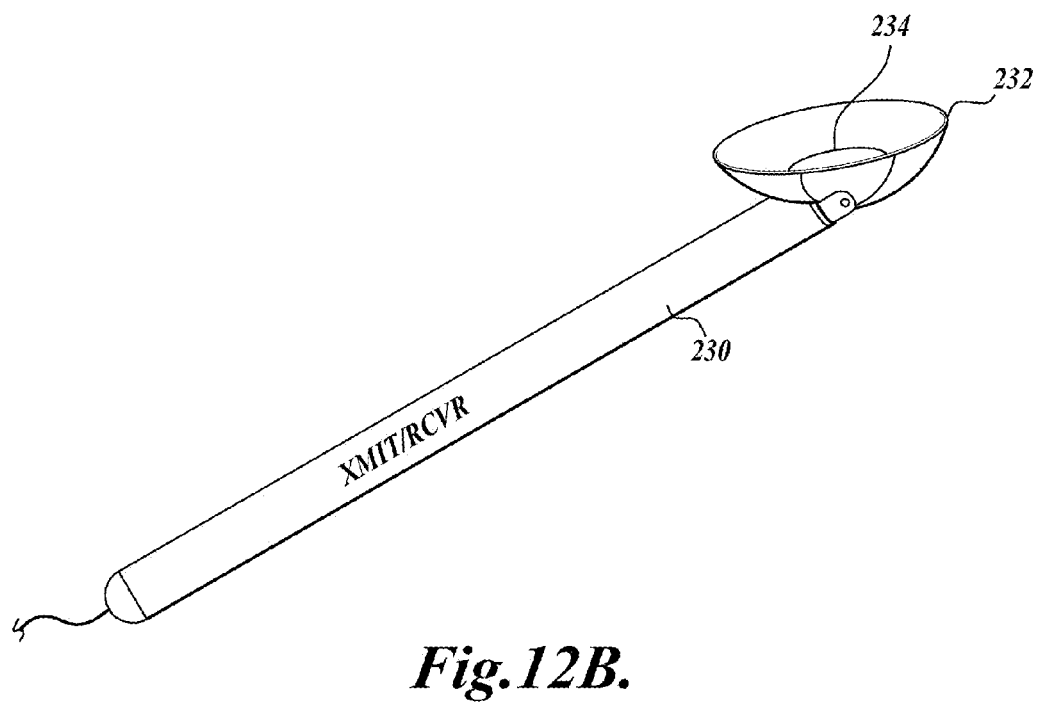

FIGS. 12A and 12B illustrate two possible applicator configurations that deliver HIFU signals to a target volume and detect echo signals at the fundamental frequency of the HIFU signal and at harmonics or other frequencies. In the example shown in FIG. 12A, a HIFU transducer probe 200 delivers one or more HIFU signals to a target volume. The HIFU transducer probe may have a fixed or variable focal point. Echo signals are received by a separate receiving transducer 220. The receiving transducer 220 has a bandwidth that is sufficient to detect echo signals over a range of frequencies that may include the fundamental frequency of the HIFU signals produced by the transducer probe 200 and its harmonics. The receiving transducer 220 may be an ultrasound imaging transducer, a non-imaging transducer such as a polyvinylidene fluoride (PVDF) transducer, a fiber optic hydrophone or other form of hydrophone. The receiving transducer 220 may be positioned to detect echo signals reflected back from the focal point. Alternatively the receiving transducer 220 may be positioned to detect signals that are transmitted through the focal point and away from the HIFU transducer.

In the example shown in FIG. 12B, a combination HIFU transmitting and receiving transducer probe 230 includes HIFU transmitting elements 232 that produce the HIFU signals and an array of higher bandwidth receiving elements 234 that are used to detect echo signals over a range of frequencies that may include the fundamental frequency of the HIFU signals and may also include one or more harmonics. The transducer in FIG. 12B may utilize a PVDF or other type of sensor.

FIGS. 13A and 13B illustrate two different feedback mechanisms to adjust a treatment parameter of a HIFU signal to be delivered. In FIG. 13A, a control signal 239 from the HIFU controller 110 is applied to a waveform generator 240 to produce a waveform of the HIFU signals that will be applied to the patient. A control signal 249 is also applied to the waveform generator 240 by a signal processing unit 248 such as a programmable microprocessor or special purpose microprocessor within the ultrasound processor 224 that correlates the transmission and receipt of HIFU signals. Alternatively, the signal processing unit 248 may be a stand-alone device. The signals from the waveform generator 240 are supplied to a pulser 242 that increases the voltage of the signals to the level required by a HIFU transducer 244 to produce ultrasound acoustic signals. Echo signals are received by the HIFU transducer 244 where they are converted back into an electronic form for supply to a receiver 246. From the receiver 246, the echo signals are supplied to the signal processing unit 248 that analyzes the echo signals in accordance with the control to determine the ratio K described above. The signal processing unit 248 produces the control signal signals 249 that are fed back to the waveform generator 240 to electronically change one or more characteristics of the HIFU signals in order to change the energy or other characteristic of the HIFU signals delivered to the patient such that the detected ratio K falls within a desired range.

The feedback mechanism shown in FIG. 13B is similar to that shown in FIG. 13A except that a separate transducer 245 is used to detect the echo or other (e.g. transmitted) signals from the patient. For example, the transducer 245 may be a high bandwidth single element transducer such as a transducer with a PVDF material, or it may be an imaging transducer. Echo or non-reflected signals received by the transducer 245 are supplied to the receiver 246 and the signal processing unit 248 that determines the value of the ratio K and what, if any, characteristics of the HIFU signals should be electronically adjusted to control the energy or other characteristic of the HIFU signals delivered to the patient.

In yet another embodiment, the system includes an integrated or separate ultrasound imaging system that produces ultrasound images such as B-mode images of the tissue. The value of the ratio K is determined for various points in the body and is color coded or otherwise made visually distinct. The visually distinguished K values in the tissue can then be combined with a B-mode or other type of ultrasound image. In one embodiment, the color coded K values 134 are overlaid onto a B-mode image on the display 132 as shown in FIG. 11. By viewing the various levels of K, the physician can see where the higher frequency components of the HIFU signals are being created. The physician can then adjust the position of the HIFU transducer probe so that the HIFU signals are being delivered into the desired area. In addition or alternatively, the physician can see if one or more characteristics of the HIFU signals should be adjusted to change the amount of energy delivered to the patient.

In another embodiment, the system may calculate the center of mass, also called a centroid, for use in the physician's on-screen display, by analyzing the harmonics received by the system. This reduces the overall clutter in the on-screen display.

In another embodiment, the system records the value of the inputs that provide the K ratio value. This allows the system to detect a correlation between pulses in order to build a successive picture of trends in feedback characteristics. This may, for example, provide information valuable in determining whether cavitation or other tissue characteristics have occurred. The system may also make use of pulse inversion in order to create a data set of K ratio values over time for use in feedback analysis that eliminates the fundamental.

Figure 14:
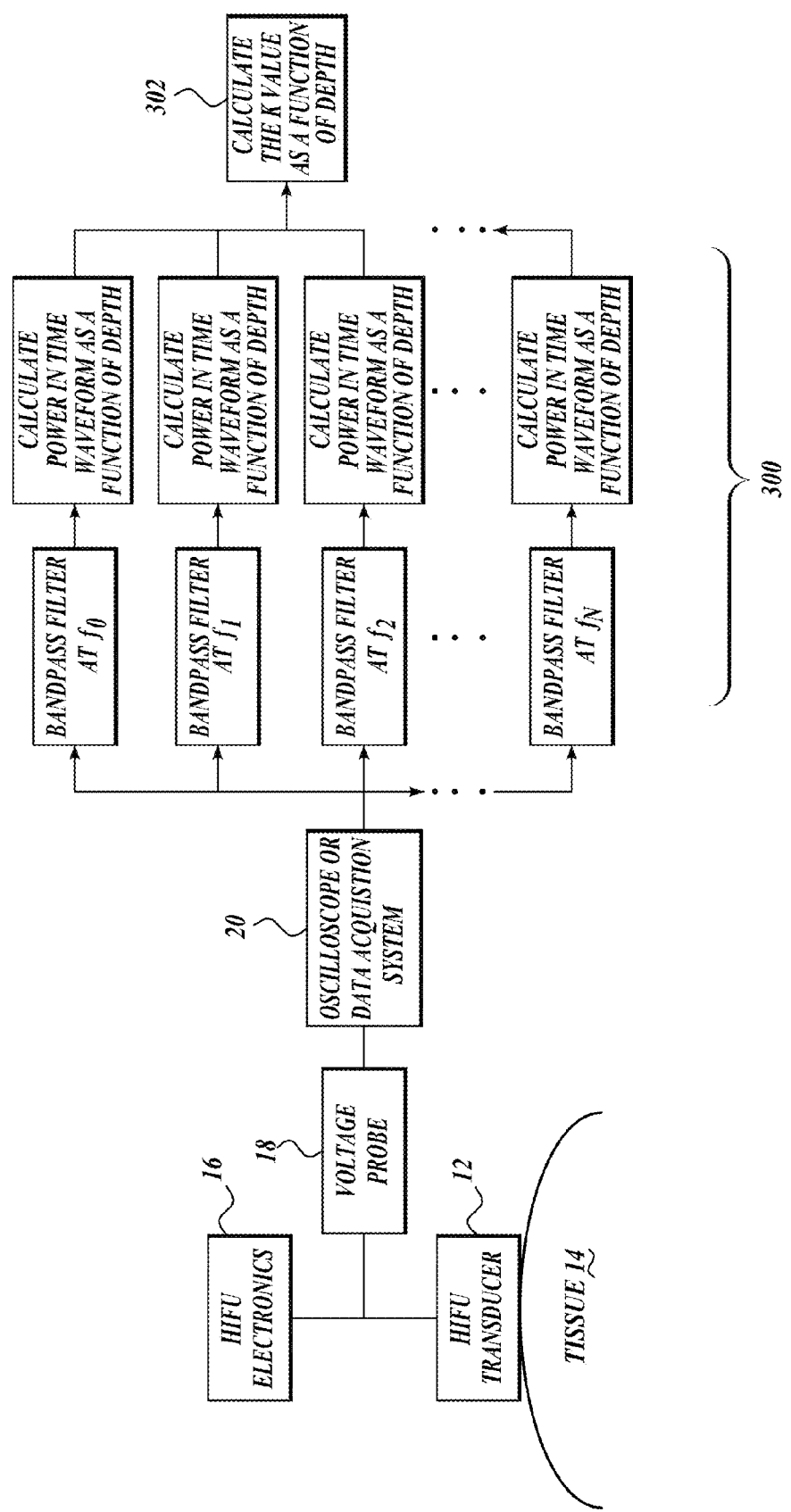
FIG. 14 illustrates a system for adjusting the delivered energy of a HIFU signal in accordance with another embodiment of the disclosed technology.

FIG. 14 illustrates another embodiment of the disclosed technology where instead of calculating the value K by Fourier transform, a number of filters 300 detect the energy of the echo signals in various frequency ranges. The filters can be digital (e.g., FIR or IIR) or analog (e.g., bandpass, notch, etc.). The value K can then be determined digitally or with an analog circuit 302.

Another possible embodiment of this technique is to use baseband detection along with low pass filtering to determine the energy in a detected signal at the fundamental as well as at one or more of the harmonics. The acquired rf vector at a particular power setting is detected and multiplied by sine and cosine waves at the fundamental or harmonic frequencies to obtain baseband data:

$$B_n(t) = x(t) * \exp(-j2\pi nft)$$

where f is either the fundamental frequency, n the order of the harmonic (e.g. n is one for the fundamental and 2 for the second harmonic), t is the time vector, x(t) is the original rf waveform, and B, is the baseband detected signal.

After mixing with the sine and cosine waves, the signal is low pass filtered to eliminate energy from other harmonics. The bandwidth of the low pass filter is driven by the bandwidth of the original excitation. After the low pass filter, the signal may be decimated to a lower sampling frequency. The baseband detected signal is associated with a specific transmit power and is a function of depth.

In addition or as an alterative to controlling treatment parameters based on the ratio of the energy in different frequency regions, other characteristics of the detected signals can also be used to select or control the treatment parameters.

Figure 15:
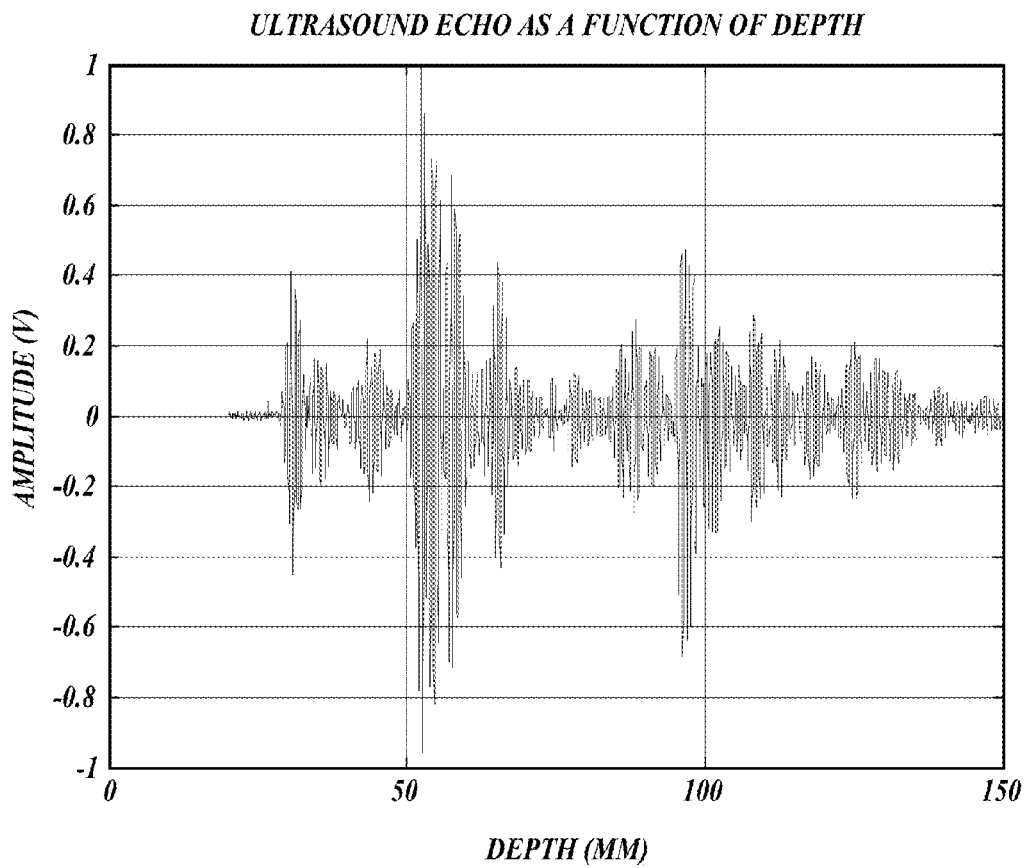
FIG. 15 illustrates the amplitude versus depth of an echo signal created in tissue as a result of a HIFU signal.
Figure 16:
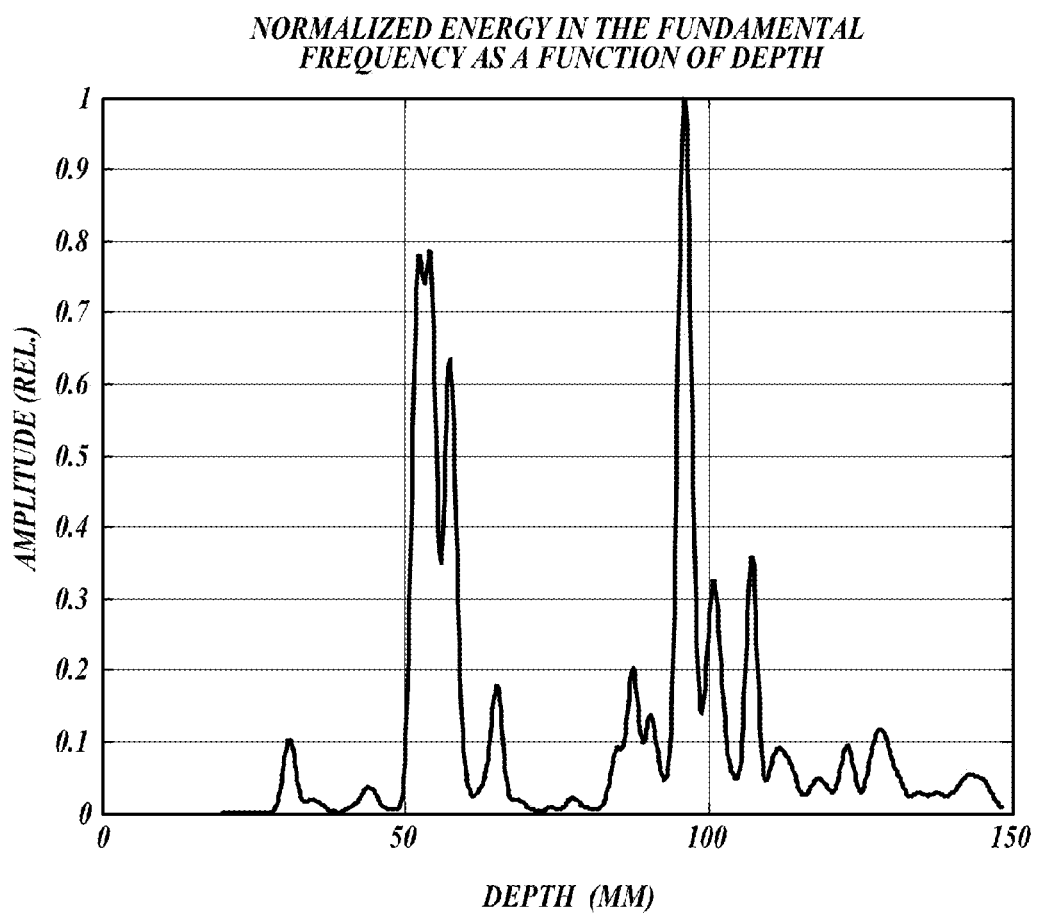
FIG. 16 is a graph of the energy in the echo signal at the fundamental frequency of the HIFU signal versus depth.
Figure 17:
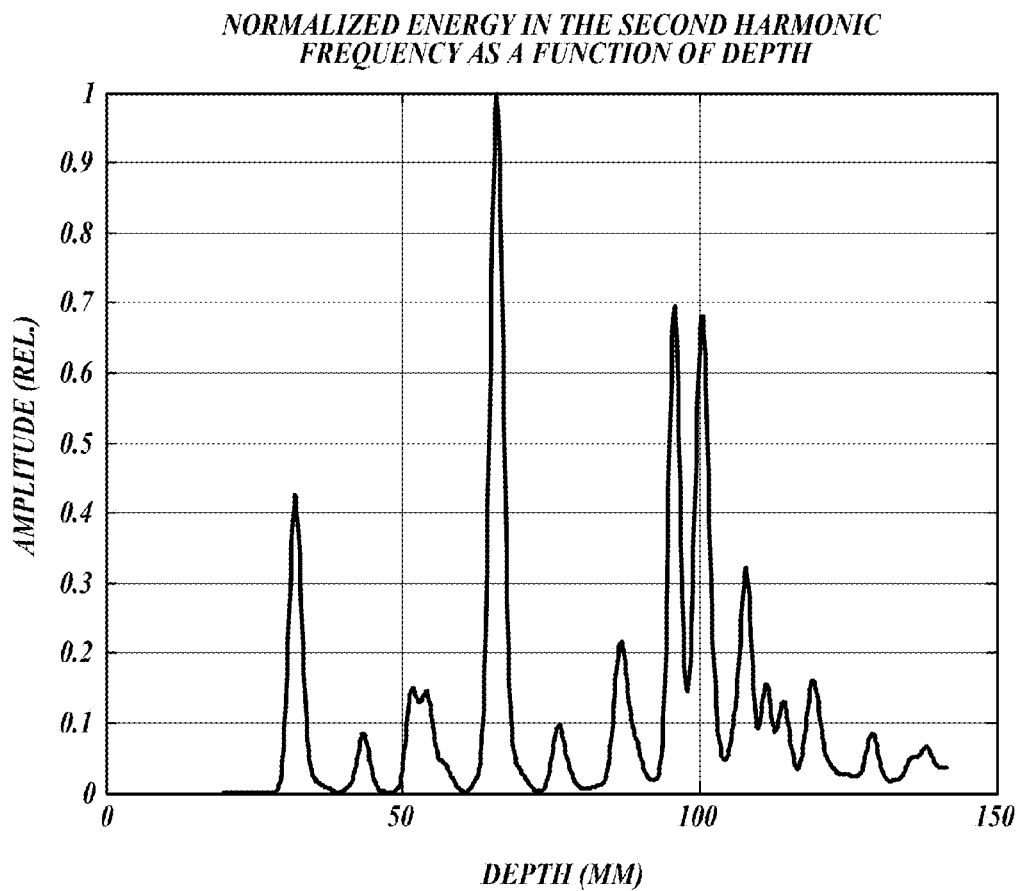
FIG. 17 is a graph of the energy in the echo signal at the second harmonic of the HIFU signal versus depth.
Figure 18:
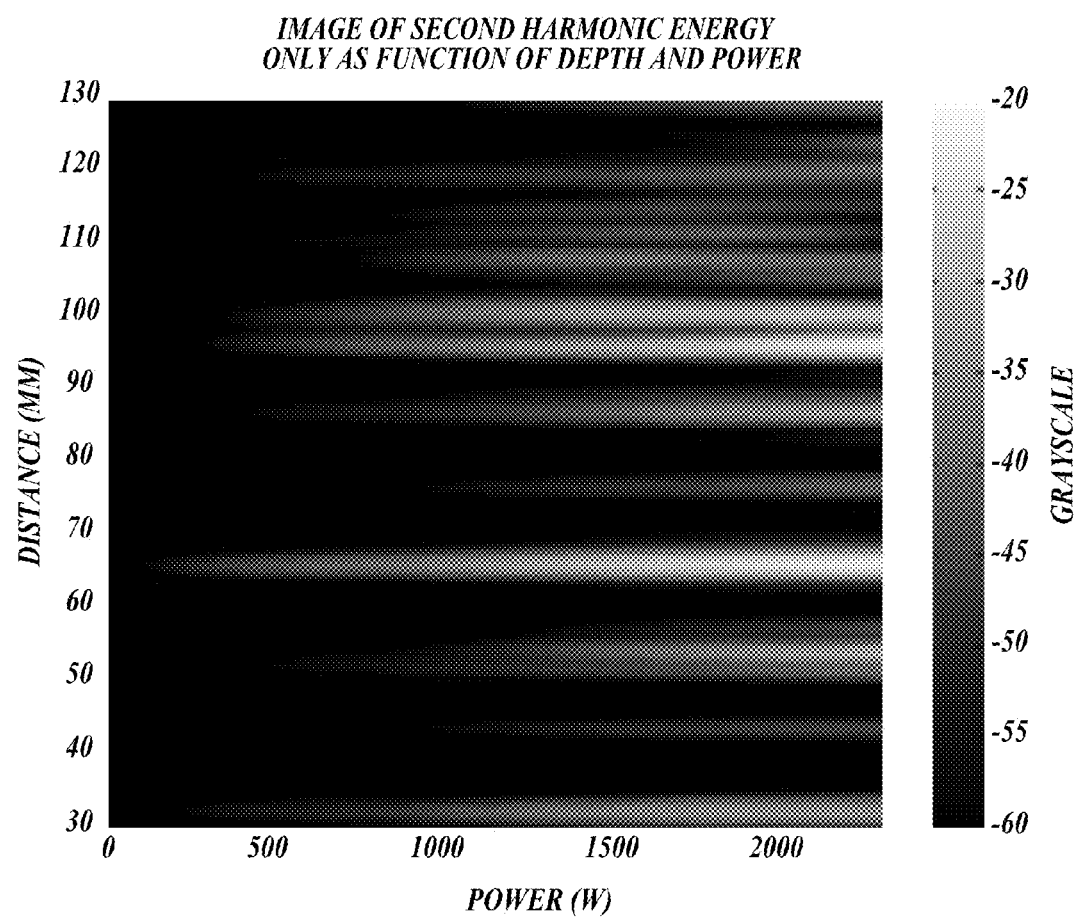
FIG. 18 is a two dimensional plot of the energy in the echo signal at the second harmonic of the HIFU signal versus depth and power level of a HIFU signal.

FIG. 15 shows an original ultrasound echo obtained from an in-vivo porcine subject in which a HIFU signal was targeted at 107 mm. FIGS. 16 and 17 show the baseband detected signals for the fundamental and second harmonic of the echo signal respectively. As more signals are acquired at different power levels, a filter may be applied over the ensemble of detected signals to reduce noise artifacts. Furthermore, additional filtering in depth and power dimension may be applied due to the expected transitions. FIG. 18 shows a 2D image of the second harmonic energy as a function of depth and excitation power. To select a treatment parameter such as the desired transmit power, a search region may be defined around the expected focus. The size of the search region will vary depending on the depth-of-field of the transducer and potential variances in propagation velocity.

Figure 19:
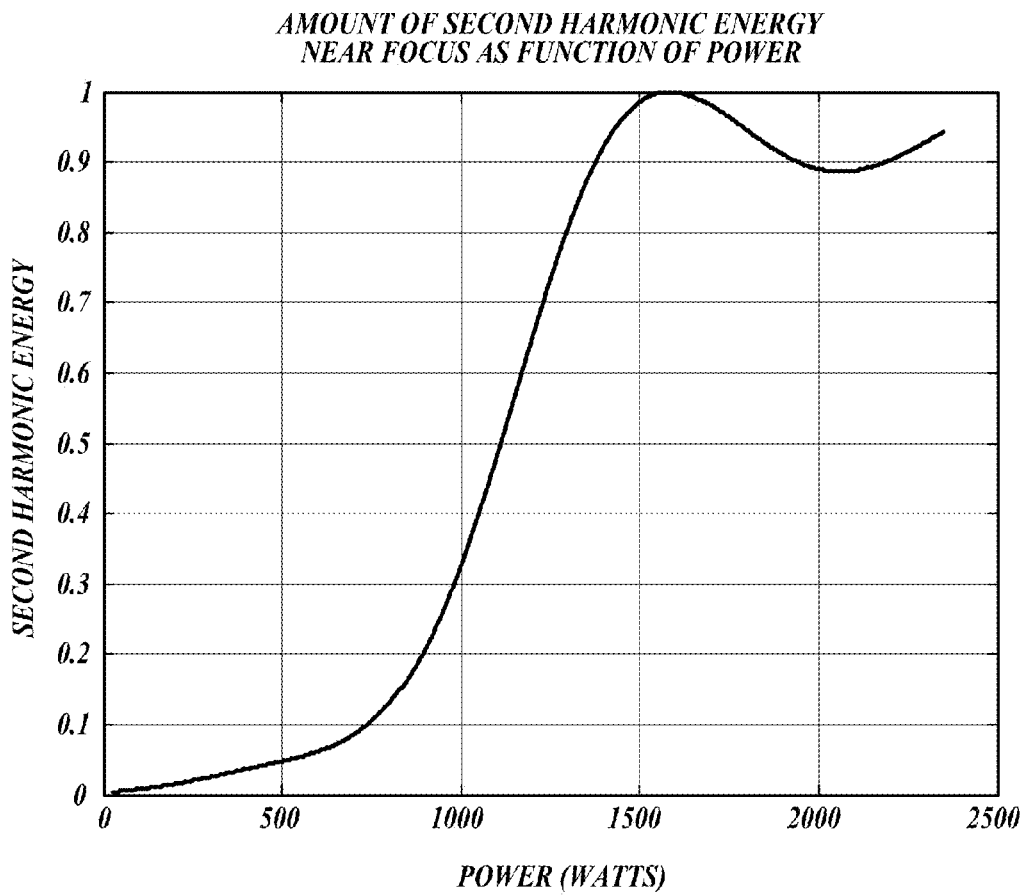
FIG. 19 is a plot of the energy in the echo signal at the second harmonic of the HIFU signal versus the power level of a HIFU signal.

As will be described below, the response of a signal characteristic to changes in the power of a transmitted HIFU signal is used to select one or more treatment parameters of HIFU signals that will be used to treat a tissue site. FIG. 19 illustrates a response curve showing how the energy of a received signal at the second harmonic of the HIFU test signals varies with changes in HIFU power for a tissue area near the focal point of the transducer. Depending on how many test signals are used, the response curve would be created from a series of discrete data points obtained for different transmit powers that are then mathematically smoothed.

In the example shown, the response curve shown in FIG. 19 is computed from received echo signals at the second harmonic of the HIFU transmit frequency. However it will be appreciated that the signal detected could be a signal that passes through the treatment site or could be computed for another harmonic or range of frequencies or combination of harmonics. In general, the response curve will be computed for a signal characteristic that exhibits a measurable change with changes in transmitted HIFU power.

In one embodiment, to select the one or more treatment parameters to be used in treating a tissue site, the response curve for the tissue is determined using a number of test signals transmitted at different power levels. The response curve may be compared to previously known response curves having treatment parameters associated with them. The treatment parameters associated with the previously known response curve that best matches the response curve for the tissue site in question can be used to treat the tissue site. Alternatively, one or more points on the response curve for the tissue can by analyzed to select the one or more treatment parameters.

In one embodiment, the response curves can be analyzed to determine a saturation point, slope or other characteristic such as the shape of the curve. FIG. 19 shows a saturation point for the second harmonic signal near the focus with a power saturation value of approximately 1500 W. The treatment parameters associated with a 1500 watt saturation point can therefore be used to treat the tissue.

To automate the determination of the saturation levels in the focal region the response curve is analyzed with a suitably programmed processor or computer. In one embodiment, the goal is to identify the power which exhibits the highest level of scattered energy and thus energy absorption. Ideally regions with significant amounts of harmonic energy would be used to maximize signal-to-noise ratio. For example, the peaks throughout the search region may be selected rather than each sample.

In one embodiment, a look-up-table (LUT) of expected response curves is used to determine the saturation values around the focus. This LUT may consist of response curves predicted theoretically with different characteristics such as attenuation and isentropic non-linearity parameter B/A. Statistical techniques such as correlation are used to compare the theoretical curves to the detected response curve. In this case, it is possible to obtain the saturation power as well as the effective characteristics of the tissue path such as attenuation that can be used to determine the length of treatment time to treat the tissue site.

In another embodiment, the processor or computer is programmed to determine the first and second derivatives of the determined response curve. Next, regions that are concave down with both positive and negative slopes on either side are identified and considered the saturation value.

In yet another embodiment, the expected first and second derivatives are used to code the waveform at a particular depth. Rather than look for a place that has a slope of zero and is concave down, the processor or computer is programmed to use other characteristics of the expected curve predicted by theory or other controlled experiments to increase the confidence that the correct saturation value was chosen. A code is assigned to the expected waveform and the code of the experimental data is determined based on the sign of the first and second derivative. For example, a code of zero is assigned to a slope of zero, a code of one to a negative slope and code of two to a positive slope. In this case, each point analyzed on the response curve could have one of nine possible codes (e.g. 00, 01, 02, 10, 11 etc.). The code is modified only if there is a change between the value of the first and second derivatives between samples, which further compresses the data. A correlation value may be determined between the coded expected value and the coded experimental value to increase the reliability of the algorithm. If the correlation is not above a certain value, then the saturation cannot be determined.

In some embodiments, the curve with the lowest saturation value is used as the prediction. Another method is to average the results through the search region and utilize this for treatment. Ideally, the process for determining the saturation value occurs in real-time such that exorbitant power values are not used.

This idea may be extended to lesions at different depths. In this case, interrogations at different lesion locations are completed. The estimated saturation levels are compared. This allows for the possible calculation of the effective attenuation in the treatment region.

In yet another alternative embodiment of the disclosed technology, the response curve for the detected signals that is analyzed to determine the treatment parameters is related to the temperature change at the focal zone. In this case, HIFU test signals are transmitted and a change in temperature is determined based a detected speckle shift of a reflected signal (echo) or transmitted signal. Speckle shifts are determined for a number of HIFU signals transmitted at different power levels in order to generate the response curve. Preferably the test HIFU signals are sufficiently short so that the tissue in the focal zone does not undergo sustained heating prior to treatment or between test signals. The response curve is analyzed by comparing against predetermined response curves or by determining some characteristic such as its saturation point, whereby the speckle shift no longer increases or decreases with increases in delivered HIFU signal power. Once the response curve has been analyzed either by comparison to previously determined response curves or by analyzing selected points on the response curve, the treatment parameters can be selected.

In yet another alternative embodiment, a response curve related to the dispersion of the waveform transmitted into the tissue is used to control or select the treatment parameter for the HIFU signals to be used to treat the target tissue site.

Dispersion occurs in acoustic waves and is noted by a slight velocity difference of the wavefront that is a function of frequency although the group velocity may remain constant. In high intensity acoustics, dispersion in the wave pulse naturally occurs in regions of high compression due to the production of harmonics. The high pressure and non-linearities of tissue eventually lead to acoustic shock at the highest compressional pressures. The production of harmonics and dispersion are less likely to occur in low pressure pulses. As the pressure is increased, the amount of dispersion increases since harmonics are more easily generated. This dispersion is detected as a phase shift in the waveform as the amplitude of the excitation moves from low pressure to high pressure. The dispersion is seen as movement of the rf signal toward the transducer and is localized by the area of high pressure. This is unique when compared to other effects such as acoustic radiation force (ARF) and apparent phase shifts due to temperature changes. In both of these cases, the expectation is the phase shift is away from the transducer. Furthermore, velocity changes due to temperature are an integrative effect in tissue. In other words, where the local temperature has increased, the shift will appear at that point as well as for every point behind the thermal increase.

Figure 20:
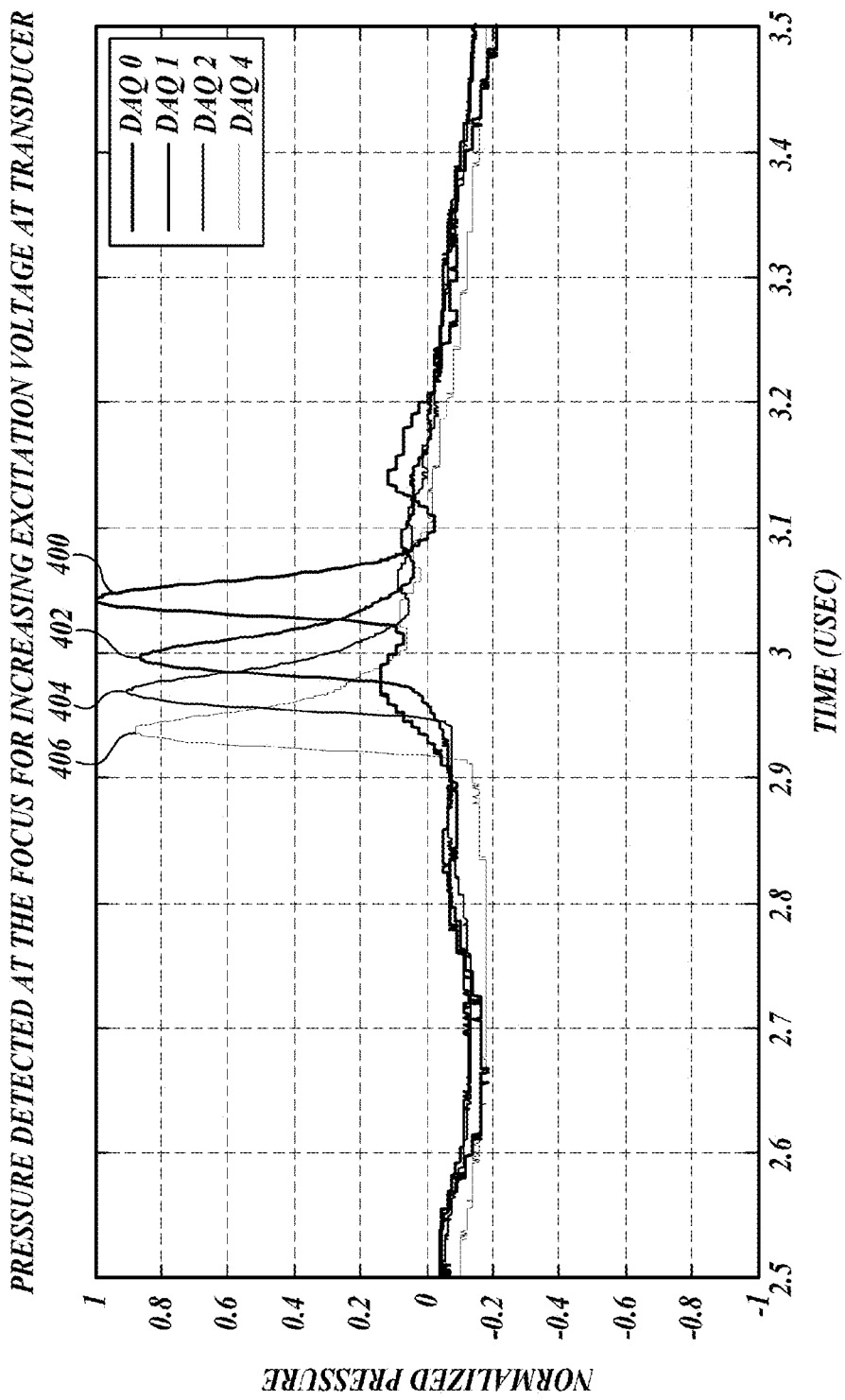
FIG. 20 is a plot of dispersion created in echo signals in response to HIFU signals transmitted at different power levels.
Figure 21:
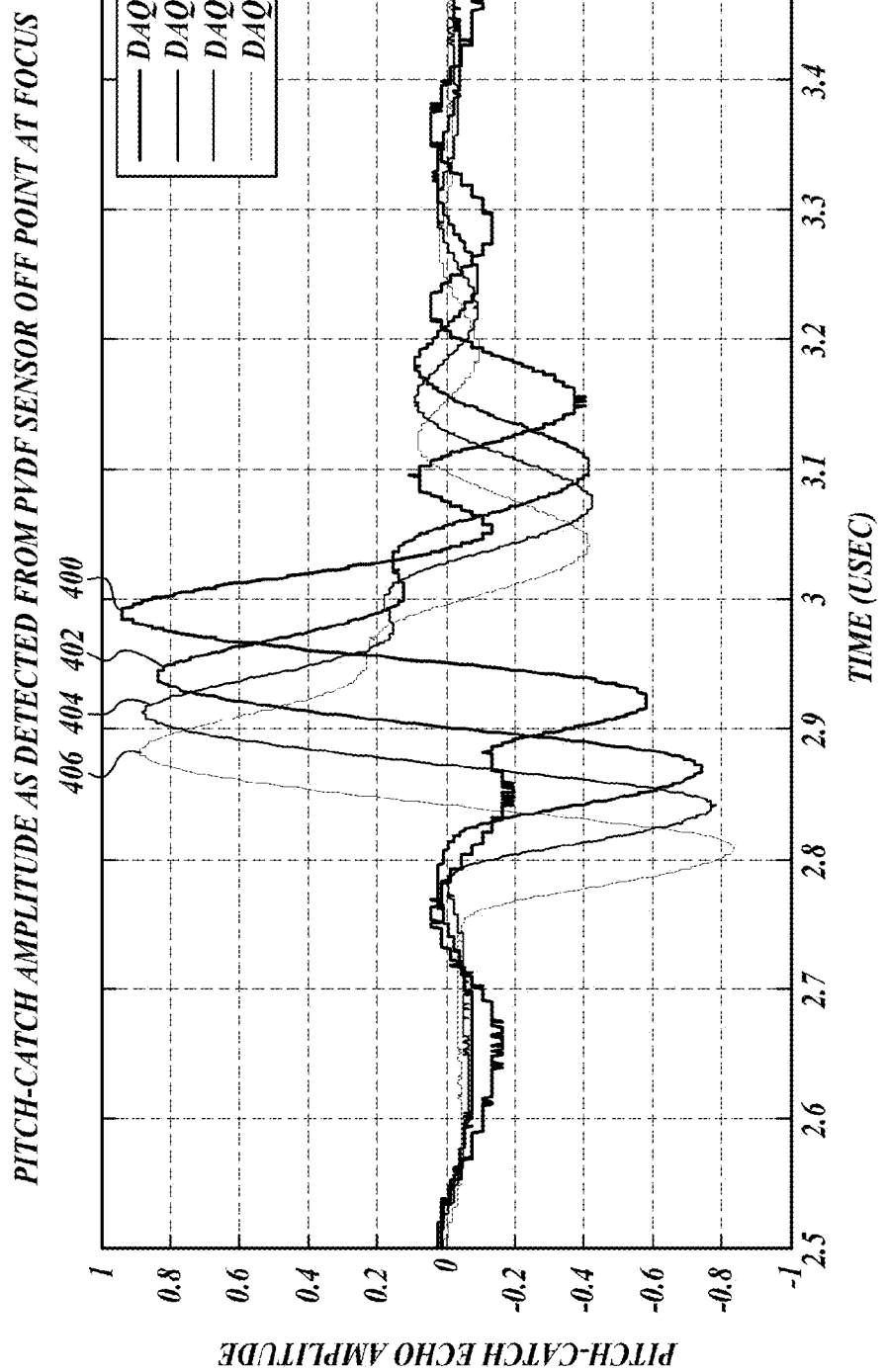
FIG. 21 is a plot of dispersion created in echo signals in response to HIFU signals transmitted at different power levels.

FIG. 20 shows the changes that occur in the pressure pulse at the focus at increasing transmit pressures 400, 402, 404, 406. Each pulse has been normalized for purposes of illustration. In this case, the fiber optic pressure hydrophone (FOPH) is receiving the transmitted pulse at the focus (in this case 64 mm). The high compressional pressure produces the shock that appears between 2.9 usec and 3.1 usec in FIG. 20. As the pressure is increased, the shock front is produced prior to the focus which yields to the detected dispersion at the focus. FIG. 20 captures the movement of the compression peak from a low excitation level (400) to a high excitation level (406). In this case, the movement is approximately 0.1 usec. FIG. 21 shows the received echo from a point target at the focus at the same transmit power levels 400, 402, 404, 406. The PVDF sensor shows dispersion occurring for negative as well as positive pressures. This is due to the PVDF sensor impulse response. When a wide bandwidth wavefront such as that shown in FIG. 21 impinges the PVDF sensor surface, the sensor will mechanically vibrate equally in compression and rarefaction.

The resulting phase shifts shown in FIGS. 20 and 21 are detected as a spatial shift in an ultrasound image. This spatial shift may be detected on rf as well as detected data. Furthermore, the detected phase shift may be used to localize areas of high pressure. Therefore, it is possible to create a pressure map of the body based on dispersion.

Dispersion may be detected as a slight shift in the image or speckle toward the HIFU transducer as test signals of successively higher power are applied to the tissue. This is illustrated in FIGS. 20 and 21 in which the higher level DAQ settings correspond to higher power levels and the time to receive the wavefront corresponds to its position relative to the transducer.

As the power level is increased, there is a corresponding increase in production of harmonics at the focal region—which in turn reduces the time to receive the signal scattered from the focal region, due to dispersion. This reduced time can be perceived as a spatial shift in the ultrasound image towards the transducer, assuming the signals are displayed graphically.

Figure 22:
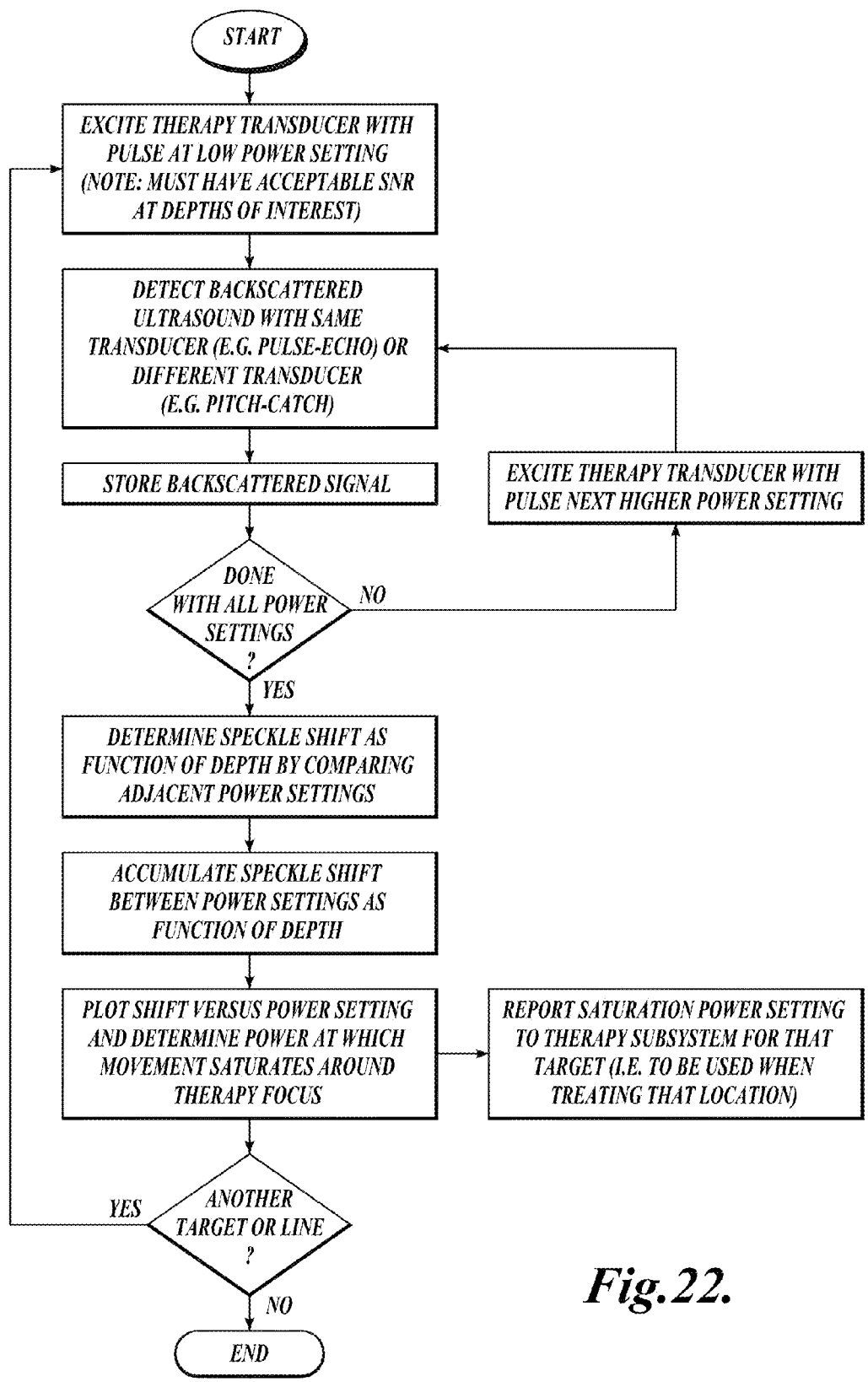
FIG. 22 is a flowchart of steps performed to select a power level for HIFU signals to be used to treat a tissue site in accordance with an embodiment of the disclosed technology.

As shown in the attached flowchart of FIG. 22, to determine a treatment parameter such as a power level setting for HIFU to be delivered to a tissue treatment site, a therapy transducer is briefly excited at a number of test power level settings. At each such setting, a backscattered ultrasound signal is detected with the same transducer that delivers the signals or with a different transducer. The backscattered signals are stored until each of the possible power levels are tested or until an optimal power level is determined.

After delivering the test signals with the different power level settings, the speckle shift associated with adjacent power level settings is determined. A response curve showing the change in the speckle shift versus changes in HIFU power is created with a programmed processor or computer. The response curve is analyzed and used to select one or more treatment parameters. For example, a programmed processor can analyze the response curve to determine a power level at which the speckle shift saturates i.e. doesn't change with further increases in power or the amount of speckle shift decreases with further increased power. In one embodiment, the treatment parameters are selected based on the power level of the HIFU that causes saturation. Other signals characteristics such as the slope of the response curve can be used to select the treatment parameters. In yet another alternative embodiment, the response curve can be compared with predefined response curves having treatment parameters associated with them. The treatment parameters associated with the response curve that best matches the determined response curve can be used to treat the tissue.

In one embodiment, treatment of each location within an intended treatment volume may be immediately preceded by determination of the treatment parameters for that location. In another embodiment, the treatment parameters may be determined at a variety of locations within an intended treatment volume prior to commencing treatment of any such location. The treatment parameters for each location are then stored in a memory or other computer readable media. Once treatment begins, the selected treatment parameters are recalled for each such location and used to treat that location. In yet another embodiment, the treatment parameters selected for one location can be used to treat an entire volume of tissue.

To maximize the accuracy and consistency of this method for selecting treatment parameters, the successive test HIFU signals should be spaced together closely in time so as to minimize any spatial shifts that might occur due to tissue motion (e.g. due to breathing or other patient motion).

In addition, the test signals should be applied in a manner which minimizes local heating of tissue, so as to avoid shifts that might occur due to changes in local sound velocity.

In yet another embodiment, the energy in a received signal at harmonics of the fundamental frequency of the HIFU signal can be estimated by measuring the energy at the fundamental frequency. This technique allows a more narrow band detection system to be used.

If a HIFU signal is delivered to the tissue at power $P_1$ (that is selected to be low enough not to create energy at the harmonics in the tissue) and at a distance r, the HIFU signal will produces a signal with energy at the fundamental frequency of the HIFU signal that is defined by a function:

$$Xf(P1, r) \quad (6)$$

If the tissue behaved linearly, then the energy at the fundamental of a signal created from a HIFU signal that is transmitted at a higher power level $P_2$, should be related to the different power level by the function:

$$Xf(P2, r) = \frac{P2}{P1} Xf(P1, r) \quad (7)$$

However the tissue generally does not respond linearly to higher power levels of HIFU signals. Therefore the measured energy at the fundamental frequency of a signal that is created in response to a higher power HIFU signal will differ from the prediction. The difference is related to the energy that is being converted into the energy at the harmonics.

To estimate the energy at the harmonics, the energy of a received signal at the fundamental frequency of the HIFU signal that is delivered at a power level $P_2$ is determined. The difference between the energy measured and the energy predicted is calculated. according to the function:

$$Xh = \frac{P2}{P1} * Xf(P1, r) - Xf(P2, r) \quad (8)$$

where Xh is the energy at the harmonics. The ratio of the energy in the harmonics to the energy at the fundamental frequency of the HIFU signals is therefore given by the function:

$$\frac{Xh(P2, r)}{Xf(P2, r)} = \frac{\frac{P2}{P1} Xf(P1, r)}{Xf(P2, r)} - 1 \quad (9)$$

A response curve can therefore be created that relates the energy of the harmonics to increases in the energy of the HIFU signals delivered. The response curve can be analyzed by a programmed processor or computer and used to select the treatment parameters either by comparison against predetermined response curves having treatment parameters associated therewith or by analyzing characteristics of the response curve and selecting treatment parameters associated with the characteristics.

In yet another embodiment, the "focal gain" i.e. the increased energy absorption caused by the energy level of the harmonics that is created in the tissue can be estimated by comparing the energy of the signals created from HIFU signals at different powers. If the tissue were linear, then the following relationship should hold for different HIFU power levels.

$$\frac{X(P2, r)}{\frac{P2}{P1} X(P1, r)} = 1 \quad (10)$$

However as the power level increases, more energy is transferred to the harmonics and the ratio should become less than one with a drop in the detected energy at the HIFU power level that causes a saturation if measured with a narrow band receiver or a gain in the detected energy at the energy level that causes saturation if measured with a wide band receiver. Therefore, a response curve can be determined that relates the ratio of detected energy to predicted energy at several different HIFU power levels. The response curve can then be analyzed or compared to other response curves in order to select one or more treatment parameters.

As will be appreciated by those skilled in the art, the deposition of energy at a treatment site is effected by the tissue's "alpha" value that is related to attenuation as well as its "B/A" value that is related to the tissue's isentropic non-linearity parameter B/A.

The alpha value for the tissue treatment site can be estimated by measuring the energy of a signal created in response to a test HIFU signal at a fixed power. The transducer can then be moved away from the treatment site and the space filled with a medium of known attenuation e.g. water. A second test HIFU signal is then applied to the tissue and the energy detected. A response curve in this example therefore relates the difference in energies detected and the distance that the transducer was moved. From the estimated attenuation of the tissue, a treatment regimen (power and treatment duration or other treatment parameter) can be selected based on predetermined clinical data performed on tissue types with similar alpha values. The alpha value for the tissue can be determined by comparing response curves for different spatial locations in the tissue.

The B/A value for a tissue site to be treated can be estimated based on comparison of the tissue's response curve with response curves computed for tissue types with known B/A values.

As indicated above, the treatment parameters such as power level, pulse duration, pulse repetition frequency etc. are selected based on an analysis of the response of the tissue to be treated to a HIFU pulse. The particular values for these treatment parameters will be based on clinical data and stored in a manner that can be indexed based on an analysis of the response curve for the treatment site. The parameter data is typically stored in a computer readable media, hard drive, CD ROM, solid state memory etc, that is accessed by a local or remote computer. When needed, the recalled treatment parameters are applied to the HIFU control hardware so that the tissue can be treated.

Figure 23:
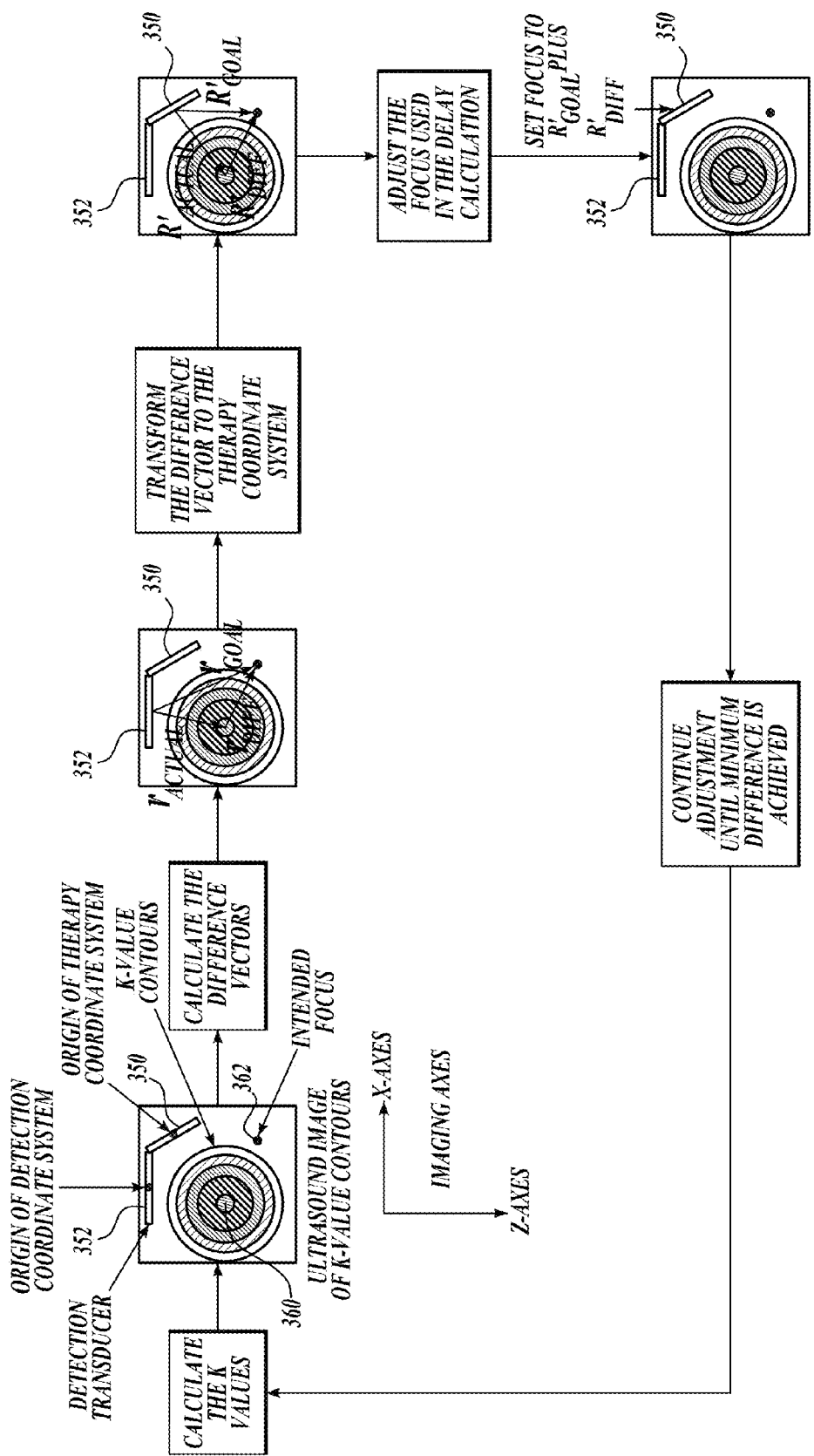
FIG. 23 illustrates a system for adjusting a focus point of a delivered HIFU signal in accordance with another aspect of the disclosed technology.

In addition or as an alternative to selecting or adjusting the energy of the delivered HIFU signals, the disclosed technology can be used to redirect the focus point of the delivered signals. In the embodiment shown in FIG. 23, a therapy transducer 350 delivers a number of test signals to a tissue site at the same or different power levels. A detection transducer 352 receives the corresponding echo or other signals, which are provided to a processor (not shown) that computes response curves, such as the K values described above or response curves based on other signal characteristics, at a number of positions in the tissue. In the example shown, the K values have a maximum value at a point 360 which is offset from an intended focus point 362 of the test signals. By comparing the location of the maximum K value to the intended focus point, the processor can determine if the focus point is misaligned. By computing the offset between the location of the maximum K value at 360 and the intended focus point at 362, a difference vector can be determined and the difference vector supplied to a beam forming equation used by a waveform generator to cause the therapy transducer 350 to redirect the focus point of the HIFU process towards the desired focus point 362. Alternatively, the difference vector can be supplied to a mechanical mechanism (not shown) that physically reorients the focus of the HIFU transducer. The process can continue by continuing to measure K values from the received echo signals and computing the location of the maximum K value and comparing it to the desired focus point until such time as the maximum K value is within a predetermined distance of the desired focus point.

If the response curves are created based on other signal characteristics, the focus can be redirected based on the response curves determined for each of the spatial locations.

Although illustrative embodiments of the disclosed technology have been illustrated and described, it will be appreciated that various changes can be made therein without departing from the scope of the technology. For example, the response curves may also be produced for a change in acoustic radiation force (ARF) that relates movement of the tissue to changes in power of the test signals. In addition, the disclosed technology is not limited to the delivery of HIFU signals to the patient but can be applied to the delivery of any waveform such as non-focused ultrasound to a non-linear medium such as tissue. Therefore, the scope of the technology is to be determined solely by the following claims and equivalents thereof.

The invention claimed is:

1. A method of operating a high intensity focused ultrasound (HIFU) system to treat a target treatment site, the method comprising:
transmitting two or more test signals into a tissue site, wherein two or more of the test signals are transmitted at different power levels at a fundamental frequency;
detecting signals from an area of the tissue site, wherein the detected signals result from transmission of the two or more test signals into the tissue site;
determining one or more response curves for the tissue site that indicate how a signal characteristic of the detected signals changes in response to the different power levels of the two or more test signals, wherein at least one of the response curves relates how energy in the test signals transfers from the fundamental frequency to one or more harmonics of the fundamental frequency with the different power levels of the test signals by comparing the energy of the detected signals at the fundamental frequency to the energy of the detected signals at the one or more harmonics using a computed ratio of the energy of the detected signals at the fundamental frequency to the energy of the detected signals at the one or more harmonics;
using at least one of the determined response curves to select a treatment parameter of HIFU signals that will be used to treat the target treatment site; and
applying HIFU signals with the selected treatment parameter to the target treatment site with the HIFU system.

2. The method of claim 1, wherein at least one of the response curves relates how an energy level of a detected signal at a harmonic of the fundamental frequency varies with the different power levels of the test signals.

3. The method of claim 1, wherein the two or more test signals include test signals transmitted in at least two different frequency ranges, and wherein at least one of the response curves relates how an energy level of a detected signal in the different frequency ranges varies with depth in the tissue site.

4. The method of claim 1, wherein at least one of the response curves relates how an energy level of a detected signal at the fundamental frequency varies with the different power levels.

5. The method of claim 1, wherein the two or more test signals include test signals transmitted in at least two different frequency ranges, and wherein at least one of the response curves relates how an energy level of a detected signal at the different frequency ranges varies with the different power levels.

6. The method of claim 1, wherein the two or more test signals include test signals transmitted in at least two different frequency ranges, and wherein at least one of the response curves relates how an energy level of a detected signal in a single range of frequencies varies with the different power levels.

7. The method of claim 1, wherein at least one of the response curves is used to select the treatment parameter by determining a closest match of the response curve to a number of predetermined response curves each having a treatment parameter associated therewith, and selecting the treatment parameter associated with the predetermined response curve that best matches the at least one response curve.

8. The method of claim 1, wherein at least one of the response curves is used to select the treatment parameter by determining a characteristic of the response curve and selecting a treatment parameter associated with the characteristic.

9. The method of claim 8, wherein the characteristic of the response curve is a saturation point of the response curve.

10. The method of claim 8, wherein the characteristic of the response curve is a shape of the response curve.

11. The method of claim 1, wherein at least one of the response curves relates how a dispersion of a detected signal varies with the different power levels.

12. The method of claim 1, wherein at least one of the response curves relates how a speckle shift related to changes in temperature at the target treatment site varies with the different power levels.

13. The method of claim 1, wherein more than one test signal is transmitted at a power level, and wherein each test signal transmitted at the same power level includes a pair of test signals having opposite phases.

14. A high intensity focused ultrasound (HIFU) system to treat tissue at a target treatment site, the system comprising:
an ultrasound transducer that is configured to deliver two or more test signals to a tissue site, wherein at least two of the test signals are transmitted at different power levels at a fundamental frequency;
a controller that is configured to control the ultrasound transducer to deliver the two or more test signals to the tissue site;
a receiver that is configured to detect signals from the tissue site, wherein the detected signals result from transmission of the two or more test signals into the tissue site;
a processor programmed to analyze the detected signals to determine one or more response curves for the tissue site that indicate how a signal characteristic of the detected signals changes in response to the different power levels of the two or more test signals, wherein at least one of the response curves relates how energy in the test signals transfers from the fundamental frequency to one or more harmonics of the fundamental frequency with the different power levels of the test signals by comparing the energy of the detected signals at the fundamental frequency to the energy of the detected signals at the one or more harmonics using a computed ratio of the energy of the detected signals at the fundamental frequency to the energy of the detected signals at the one or more harmonics,
wherein the ultrasound transducer is further configured, under control of the controller, to deliver HIFU signals to the target treatment site with a selectable treatment parameter, and
wherein the processor is programmed to select the treatment parameter for the HIFU signals to be used in treating the target treatment site based on at least one of the determined response curves.

15. The system of claim 14, wherein at least one of the response curves relates how an energy level of a detected signal at a harmonic of the fundamental frequency varies with the different power levels of the test signals.

16. The system of claim 14, wherein the two or more test signals include test signals transmitted in at least two different frequency ranges, and wherein at least one of the response curves relates how an energy level of a detected signal in the different frequency ranges varies with depth in the tissue site.

17. The system of claim 14, wherein at least one of the response curves relates how an energy level of a detected signal at the fundamental frequency varies with the different power levels.

18. The system of claim 14, wherein the two or more test signals include test signals transmitted in at least two different frequency ranges, and wherein at least one of the response curves relates how an energy level of a detected signal at the different frequency ranges varies with the different power levels.

19. The system of claim 14, wherein the processor is programmed to select the treatment parameter by determining a closest match of at least one of the response curves to a number of predetermined response curves each having a treatment parameter associated therewith, and selecting the treatment parameter associated with the predetermined response curve that best matches the at least one response curve.

20. The system of claim 14, wherein processor is programmed to select the treatment parameter by determining a characteristic of at least one of the response curves and selecting a treatment parameter associated with the characteristic.

21. The system of claim 20, wherein the characteristic of the at least one response curve is a saturation point of the response curve.

22. The system of claim 20, wherein the characteristic of the at least one response curve is a shape of the response curve.

23. The system of claim 14, wherein at least one of the response curves relates how a dispersion of the detected signal varies with the different power levels.

24. The system of claim 14, wherein the ultrasound transducer is configured to deliver more than one test signal at a power level, and wherein each test signal transmitted at the same power level includes a pair of test signals having opposite phases.

25. The system of claim 14, wherein the receiver is a HIFU transducer.

26. The system of claim 14, wherein the receiver is an ultrasound imaging transducer.

27. The system of claim 14, wherein the receiver is a polyvinylidene fluoride (PVDF) transducer.

28. The system of claim 14, wherein the receiver is a hydrophone.

29. The system of claim 14, wherein the processor is programmed to produce a signal to adjust the treatment parameter.

30. The system of claim 29, wherein the signal is perceptible by a human to manually adjust the treatment parameter.

31. The system of claim 29, wherein the signal is used in a feedback loop of the HIFU system to dynamically adjust the treatment parameter.

32. The system of claim 14, wherein the processor is programmed to select the treatment parameter by comparing characteristics of at least one of the response curves to threshold values.

33. A system for applying HIFU signals to a subject, the system comprising:
a HIFU controller configured to produce electronic HIFU driving signals having one or more adjustable characteristics that affect an energy of a delivered HIFU signal;
a HIFU transducer configured to receive the electronic HIFU driving signals, produce acoustic HIFU signals at a fundamental frequency, and apply the acoustic HIFU signals to tissue of a subject;
a receiving transducer configured to detect echo signals from the tissue of the subject;
a processor configured to receive the detected echo signals and compare an energy of the echo signals in a first frequency range to an energy of the echo signals in a second frequency range at a number of locations in the tissue; and
a display for displaying an image of the tissue along with an image representative of the comparison at one or more locations in the tissue,
wherein the processor is configured to compare the energy of the echo signals in the first frequency range to the energy of the echo signals in the second frequency range by computing a ratio of the energy of the echo signals in the first frequency range to the energy of the echo signals in the second frequency range, wherein the ratio of the energy of the echo signals relates how energy in the HIFU signals transfers from the fundamental frequency to one or more harmonics of the fundamental frequency, and
wherein the processor is configured to use the computed ratio of the energy of the echo signals to select a power level of the acoustic HIFU signals which adjusts the energy delivered by the HIFU signals in the tissue of the subject.

34. The system of claim 33, wherein the processor is further configured to quantify the ratio in a visually or audibly perceptible form.

35. The system of claim 34, wherein the visually perceptible form is a color code.

36. A method of adjusting a focal location of a HIFU transducer, the method comprising:
transmitting two or more test signals at different power levels into tissue at an intended focal location, wherein two or more of the test signals are transmitted at a selected frequency;
receiving echo signals at a number of spatial locations in the tissue, wherein the echo signals result from transmission of the two or more test signals into the tissue;
determining one or more response curves for the tissue at each of the spatial locations that indicate how a signal characteristic of the echo signals changes with changes in the power level of the two or more test signals, wherein at least one of the response curves relates how energy in the test signals transfers from the selected frequency to one or more harmonics of the selected frequency with the different power levels of the test signals, and wherein the one or more response curves compare energy in the echo signals resulting from a test signal transmitted at a first power level to energy in the echo signals resulting from a test signal transmitted at a second power level by computing a ratio of the energy of the echo signals at the first power level to the energy of the echo signals at the second power level;

analyzing the one or more response curves to determine an estimate of an actual focal location; and adjusting the intended focal location based on the estimate of the actual focal location.

37. The method of claim 36, wherein said adjusting the intended focal location is performed successively until a minimum required difference between the estimated actual focal location and intended focal location is achieved.

38. The method of claim 36, wherein said adjusting the intended focal location is performed successively until a maximum number of iterations is achieved.

39. A high intensity focused ultrasound (HIFU) system to treat tissue at a target treatment site, the system comprising:

an ultrasound transducer that is configured to deliver two or more test signals at a focal location, wherein the two or more test signals are transmitted at different power levels;

a controller that is operates to adjust the focal location of the ultrasound transducer;

a receiver that is configured to detect echo signals at a number of spatial locations, wherein the detected echo signals result from transmission of the two or more test signals into the spatial locations; and a processor that is programmed to analyze the detected echo signals to determine one or more response curves that indicate how a signal characteristic of the detected echo signals changes in response to the two or more test signals transmitted at the different power levels into the spatial locations, wherein at least one of the response curves relates how energy in the test signals transfers from a selected frequency to one or more harmonics of the selected frequency with the different power levels of the test signals, and wherein the one or more response curves compare energy in the echo signals resulting from a test signal transmitted at a first power level to energy in the echo signals resulting from a test signal transmitted at a second power level by computing a ratio of the energy in the echo signals at the first power level to the energy of the echo signals at the second power level, and wherein the processor is programmed to cause the controller to adjust the focal location of the ultrasound transducer based on at least one of the determined response curves.

40. A method of adjusting a focal location of an ultrasound transducer, comprising:

transmitting an ultrasound signal into tissue at an intended focal location with a first transducer;

receiving echo signals from the tissue with a second transducer;

determining the energy of the received echo signals in a first frequency range and a second frequency range;

comparing the energy of the received echo signals in the first frequency range to the energy of the received echo signals in the second frequency range by computing a ratio of the energy of the received echo signals in the first frequency range to the energy of the received echo signals in the second frequency range, wherein the ratio of the energy of the received echo signals relates how energy in the ultrasound signal at a frequency in the second frequency range transfers to one or more harmonic frequencies in the first frequency range; and using the computed ratio to adjust the focal location of the first transducer.

41. A high intensity focused ultrasound (HIFU) system to treat tissue at a target treatment site, comprising:

an ultrasound transducer that is configured to deliver a test signal to a tissue site at an intended focal location;

a controller that is operates to adjust the intended focal location of the ultrasound transducer;

a receiver that is configured to receive echo signals at a number of spatial locations in the tissue site; and a processor programmed to compare the energy of the received echo signals in a first frequency range to the energy of the received echo signals in a second frequency range for the spatial locations by computing a ratio of the energy of the received echo signals in the first frequency range to the energy of the received echo signals in the second frequency range, wherein the ratio of the energy of the received echo signals relates how energy in the test signal at a frequency in the second frequency range transfers to one or more harmonic frequencies in the first frequency range, and further use the computed ratio to adjust the focal location of the ultrasound transducer.

42. The high intensity focused ultrasound (HIFU) system of claim 41, wherein the processor determines a location of a maximum difference in the energy in the first and second frequency ranges as an estimate of an actual focal location, and causes the controller to adjust the intended focal location based on the estimate of the actual focal location.

43. The method of claim 40, further comprising:

determining a location of a maximum difference in the energy in the first and second frequency ranges as an estimate of an actual focal location; and adjusting the intended focal location based on the estimate of the actual focal location.

* * * * *